(12) United States Patent
Selmon et al.

(10) Patent No.: US 6,800,085 B2
(45) Date of Patent: Oct. 5, 2004

(54) METHODS AND APPARATUS FOR TREATING VASCULAR OCCLUSIONS

(75) Inventors: Matthew R. Selmon, Atherton, CA (US); Charles F. Milo, Atherton, CA (US); Robert L. Wynne, Pacifica, CA (US); Suresh S. Pai, Mountain View, CA (US); Kent D. Dell, Redwood, CA (US); Charles Gresl, San Francisco, CA (US); Gerald Hansen, Newark, CA (US); E. Richard Hill, III, Berkeley, CA (US)

(73) Assignee: LuMend, Inc., Redwood City, CA (US)

( * ) Notice: Subject to any disclaimer, the term of this patent is extended or adjusted under 35 U.S.C. 154(b) by 373 days.

(21) Appl. No.: 09/835,043

(22) Filed: Apr. 13, 2001

(65) Prior Publication Data

US 2001/0018596 A1 Aug. 30, 2001

Related U.S. Application Data

(63) Continuation of application No. 09/149,874, filed on Sep. 8, 1998, now Pat. No. 6,508,825, which is a continuation-in-part of application No. 08/775,264, filed on Feb. 28, 1997, now Pat. No. 5,968,064.

(51) Int. Cl.$^7$ ............................................. A61M 29/00
(52) U.S. Cl. ...................................... 606/198; 606/159
(58) Field of Search ............................ 606/1, 159, 198, 606/190; 604/104; 600/207

(56) References Cited

U.S. PATENT DOCUMENTS

| | | |
|---|---|---|
| 728,175 A | 5/1903 | Otto |
| 765,879 A | 7/1904 | Campbell |
| 832,201 A | 10/1906 | Kistler |
| 1,127,948 A | 2/1915 | Wappler |
| 1,267,066 A | 5/1918 | Flack |
| 2,621,651 A | 12/1952 | Wallace .......................... 128/4 |
| 2,854,983 A | 10/1958 | Baskin .......................... 128/349 |

(List continued on next page.)

FOREIGN PATENT DOCUMENTS

| | | |
|---|---|---|
| DE | 29 45 237 A1 | 5/1981 |
| DE | 44 29 117 A1 | 2/1996 |
| EP | 0 377 269 A1 | 7/1990 |
| EP | 0 521 595 A2 | 1/1993 |
| FR | 1585065 | 1/1970 |
| RU | 134398 | 1/1960 |
| WO | WO 83/03188 | 9/1983 |
| WO | WO 91/19528 | 12/1991 |
| WO | WO 92/08510 | 5/1992 |

(List continued on next page.)

*Primary Examiner*—Kevin T. Truong
(74) *Attorney, Agent, or Firm*—Shemwell Gregory & Courtney LLP

(57) ABSTRACT

An intravascular catheter system for the treatment of occluded blood vessels that includes tissue displacement or hinged expansion members that are movable from a closed to an open position. An actuating assembly may be provided for moving the tissue expansion members between an open and closed position to exert a substantially lateral distal end force upon the region surrounding an occluded blood vessel. The tissue expansion members may stretch apart, tear or otherwise disrupt a vascular occlusion sufficiently to create a pathway that may support the passage or placement of a guidewire or an interventional vascular device across the occlusion or obstruction. Methods of crossing or displacing a vascular occlusion are further provided that include the positioning of a vascular catheter having at least one hinged spreading member positioned at the distal region of the catheter that is responsive to directed force along the longitudinal axis of the catheter. A directed force is applied to the actuator in order to deploy the spreading member and displace a vascular occlusion creating a path to permit the passage of a guidewire or device therethrough.

15 Claims, 30 Drawing Sheets

U.S. PATENT DOCUMENTS

| | | | | |
|---|---|---|---|---|
| 3,640,270 | A | 2/1972 | Hoffman | 128/2.1 E |
| 3,667,474 | A | 6/1972 | Lapkin et al. | 128/345 |
| 4,043,323 | A | 8/1977 | Komiya | 128/4 |
| 4,355,643 | A | 10/1982 | Laughlin et al. | 128/663 |
| 4,541,433 | A | 9/1985 | Baudino | 128/668 |
| 4,572,186 | A | 2/1986 | Gould et al. | 128/341 |
| 4,585,000 | A | 4/1986 | Hershenson | 128/345 |
| RE32,158 | E | 5/1986 | Vukovic | 128/6 |
| 4,630,609 | A | 12/1986 | Chin | 128/344 |
| 4,648,402 | A | 3/1987 | Santos | 128/345 |
| 4,669,467 | A | 6/1987 | Willett et al. | 128/303.1 |
| 4,681,110 | A | 7/1987 | Wiktor | 128/343 |
| 4,698,057 | A | 10/1987 | Joishy | 604/176 |
| 4,723,549 | A | 2/1988 | Wholey et al. | 128/344 |
| 4,737,142 | A | 4/1988 | Heckele | 604/95 |
| 4,787,388 | A | 11/1988 | Hofmann | 128/344 |
| 4,794,928 | A | 1/1989 | Kletschka | 128/344 |
| 4,848,336 | A | 7/1989 | Fox et al. | 128/303.1 |
| 4,862,874 | A | 9/1989 | Kellner | 128/6 |
| 4,919,112 | A | 4/1990 | Siegmund | 128/4 |
| 5,001,556 | A | 3/1991 | Nakamura et al. | 358/98 |
| 5,002,041 | A | 3/1991 | Chikama | 128/4 |
| 5,011,488 | A | 4/1991 | Ginsburg | 606/159 |
| 5,019,040 | A | 5/1991 | Itaoka et al. | 604/95 |
| 5,030,201 | A | 7/1991 | Palestrant | 604/22 |
| 5,034,001 | A | 7/1991 | Garrison et al. | 604/53 |
| 5,089,006 | A | 2/1992 | Stiles | 606/198 |
| 5,092,839 | A | 3/1992 | Kipperman | 604/53 |
| 5,098,381 | A | 3/1992 | Schneider | 604/96 |
| 5,099,850 | A | 3/1992 | Matsui et al. | 128/662.06 |
| 5,100,425 | A | 3/1992 | Fischell et al. | 606/159 |
| 5,102,390 | A | 4/1992 | Crittenden et al. | 604/96 |
| 5,114,414 | A | 5/1992 | Buchbinder | 604/95 |
| 5,156,594 | A | 10/1992 | Keith | |
| 5,179,961 | A | 1/1993 | Littleford et al. | 128/772 |
| 5,180,368 | A | 1/1993 | Garrison | 604/104 |
| 5,192,290 | A | 3/1993 | Hilal | 606/159 |
| 5,193,546 | A | 3/1993 | Shaknovich | 128/662.06 |
| 5,197,971 | A | 3/1993 | Bonutti | 606/192 |
| 5,209,729 | A | 5/1993 | Hofmann et al. | 604/96 |
| 5,211,654 | A | 5/1993 | Kaltenbach | 606/191 |
| 5,217,484 | A | 6/1993 | Marks | 606/200 |
| 5,263,959 | A | 11/1993 | Fischell | 606/180 |
| 5,263,963 | A | 11/1993 | Garrison et al. | 606/198 |
| 5,263,967 | A | 11/1993 | Lyons, III et al. | |
| 5,279,565 | A | 1/1994 | Klein et al. | 604/105 |
| 5,282,817 | A | 2/1994 | Hoogeboom et al. | 606/167 |
| 5,304,199 | A | 4/1994 | Myers | 606/194 |
| 5,321,501 | A | 6/1994 | Swanson et al. | 356/345 |
| 5,334,210 | A | 8/1994 | Gianturco | 606/151 |
| 5,336,252 | A | 8/1994 | Cohen | 607/119 |
| 5,350,377 | A | 9/1994 | Winston et al. | 606/15 |
| 5,351,678 | A | 10/1994 | Clayton et al. | 126/6 |
| 5,383,467 | A | 1/1995 | Auer et al. | 128/664 |
| 5,409,453 | A | 4/1995 | Lundquist et al. | 604/22 |
| 5,415,636 | A | 5/1995 | Forman | 604/101 |
| 5,423,846 | A | 6/1995 | Fischell | 606/180 |
| 5,439,000 | A | 8/1995 | Gunderson et al. | 128/664 |
| 5,456,667 | A | 10/1995 | Ham et al. | 128/664 |
| 5,459,570 | A | 10/1995 | Swanson et al. | 356/345 |
| 5,484,412 | A | 1/1996 | Pierpont | 604/101 |
| 5,486,170 | A | 1/1996 | Winston et al. | 606/16 |
| 5,486,193 | A | 1/1996 | Bourne et al. | 606/194 |
| 5,490,859 | A | 2/1996 | Mische et al. | 606/159 |
| 5,493,000 | A | 2/1996 | Aharoni | |
| 5,499,995 | A | 3/1996 | Teirstein | 606/192 |
| 5,501,694 | A | 3/1996 | Ressemann et al. | 606/159 |
| 5,507,295 | A | 4/1996 | Skidmore | 128/662.06 |
| 5,507,296 | A | 4/1996 | Bales et al. | 128/751 |
| 5,511,559 | A | 4/1996 | Vance | 128/772 |
| 5,522,819 | A | 6/1996 | Graves et al. | 606/113 |
| 5,540,707 | A | 7/1996 | Ressemann et al. | 606/159 |
| 5,556,408 | A | 9/1996 | Farhat | 606/180 |
| 5,569,298 | A | 10/1996 | Schnell | |
| 5,573,531 | A | 11/1996 | Gregory | 606/14 |
| 5,599,306 | A | 2/1997 | Klein et al. | 604/96 |
| 5,618,300 | A | 4/1997 | Marin et al. | 606/198 |
| 5,626,599 | A | 5/1997 | Bourne et al. | 606/194 |
| 5,626,607 | A | 5/1997 | Malecki et al. | 606/205 |
| 5,632,746 | A | 5/1997 | Middleman et al. | 606/78 |
| 5,649,941 | A | 7/1997 | Lary | 606/159 |
| 5,653,684 | A | 8/1997 | Laptewicz et al. | 604/22 |
| 5,662,671 | A | 9/1997 | Barbut et al. | 606/170 |
| 5,683,451 | A | 11/1997 | Lenker et al. | |
| 5,688,234 | A | 11/1997 | Frisbie | 604/22 |
| 5,695,515 | A | 12/1997 | Orejola | 606/191 |
| 5,707,390 | A | 1/1998 | Bonutti | 606/204 |
| 5,713,907 | A | 2/1998 | Hogendijk et al. | 606/108 |
| 5,752,973 | A | 5/1998 | Kieturakis | |
| 5,762,613 | A | 6/1998 | Sutton et al. | 600/564 |
| 5,766,151 | A | 6/1998 | Valley et al. | |
| 5,800,450 | A | 9/1998 | Lary et al. | 606/180 |
| 5,816,923 | A | 10/1998 | Milo et al. | 464/58 |
| 5,893,875 | A | 4/1999 | O'Connor | |
| 5,964,779 | A | 10/1999 | Mayenberger | |
| 5,968,064 | A | 10/1999 | Selmon et al. | |
| 6,010,449 | A | 1/2000 | Selmon et al. | |
| 6,015,423 | A | 1/2000 | Andrese | 606/198 |
| 6,120,516 | A | 9/2000 | Selmon et al. | |
| 6,217,549 | B1 | 4/2001 | Selmon et al. | |
| 6,398,798 | B2 | 6/2002 | Selmon et al. | |
| 6,436,119 | B1 | 8/2002 | Erb et al. | |
| 6,508,825 | B1 | 1/2003 | Selmon et al. | |
| 6,520,973 | B1 | 2/2003 | McGarry | |

FOREIGN PATENT DOCUMENTS

| | | | |
|---|---|---|---|
| WO | WO 93/18818 | 9/1993 | |
| WO | WO 95/19143 | 7/1995 | |
| WO | WO 96/01590 | 1/1996 | |
| WO | WO 96/11636 | 4/1996 | |
| WO | WO 98/40015 | 9/1998 | A61B/10/00 |
| WO | WO 99/23957 | 5/1999 | A61B/17/22 |
| WO | WO 99/40963 | 8/1999 | |
| WO | WO 00/20064 | 4/2000 | A61M/25/01 |

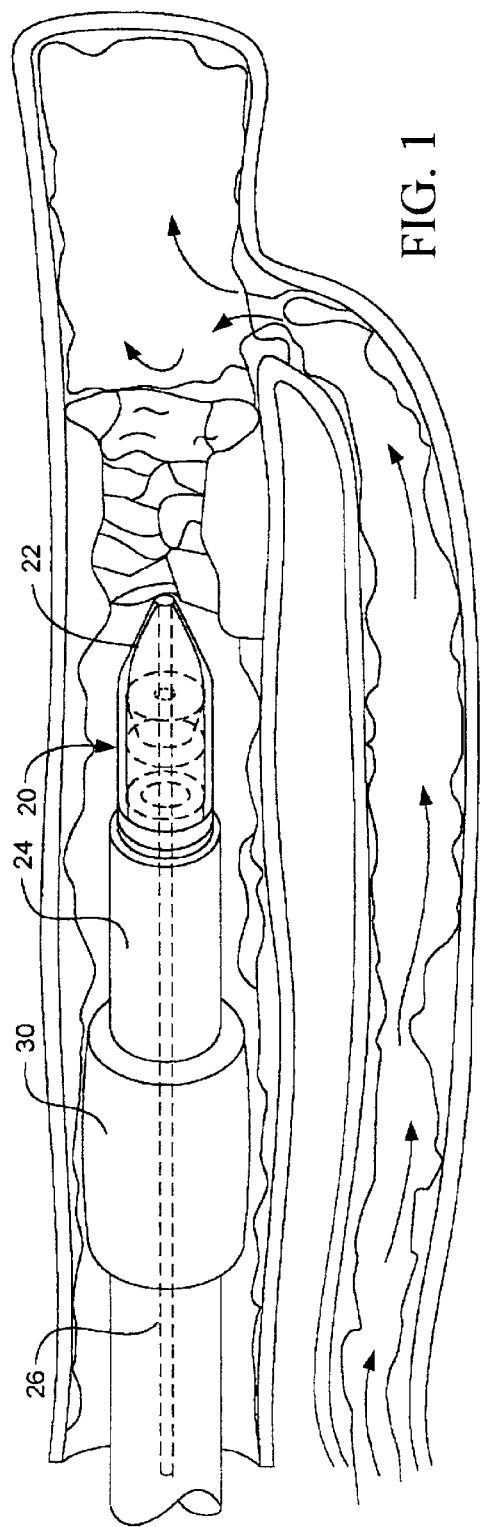
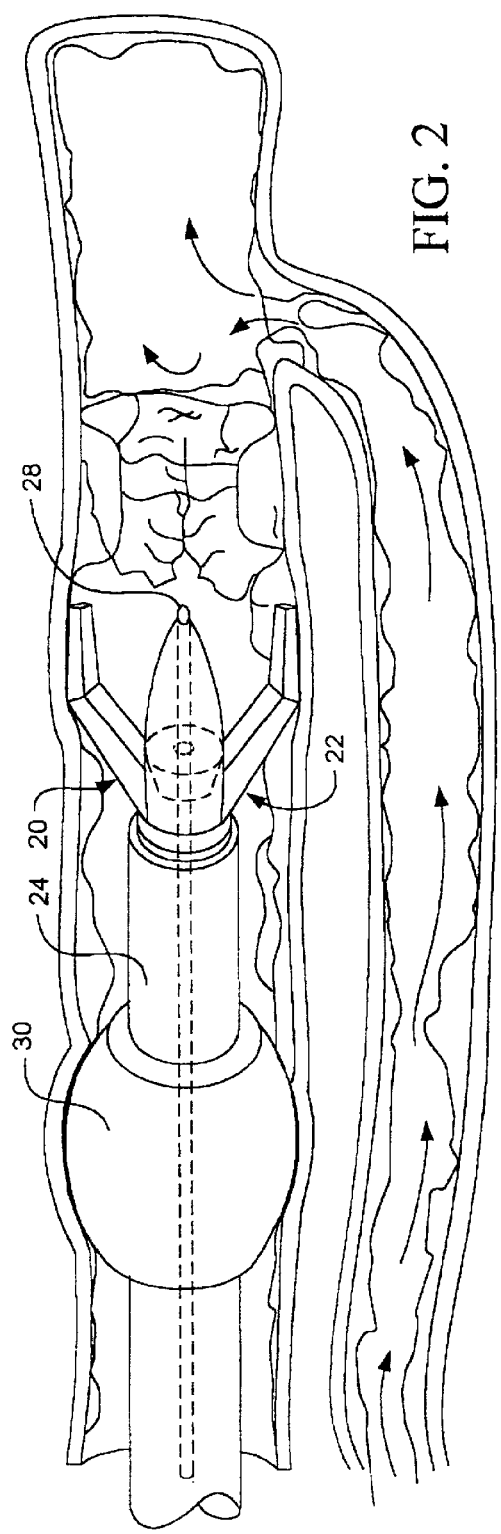

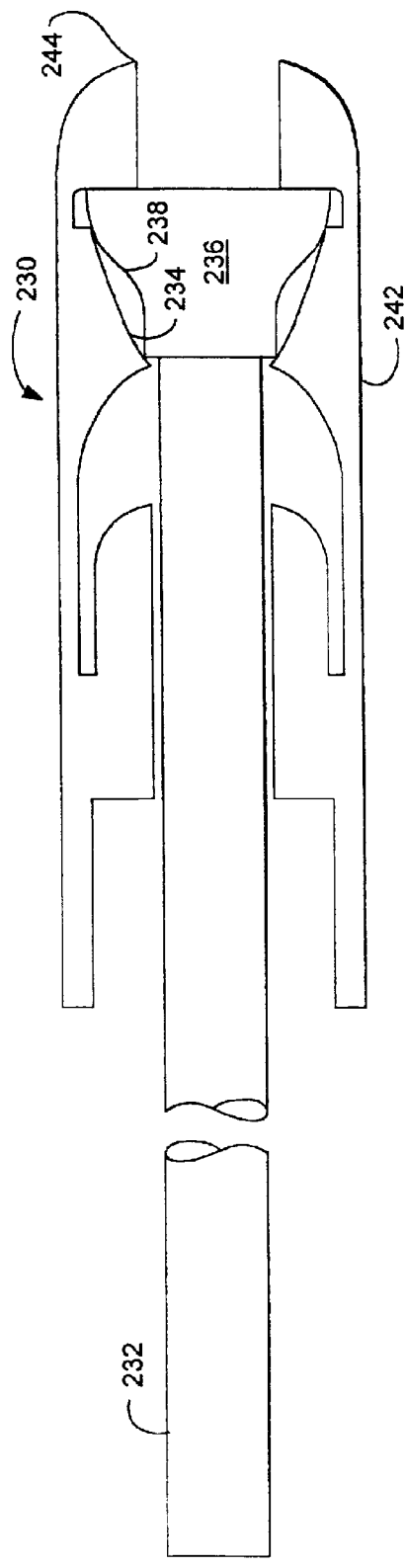
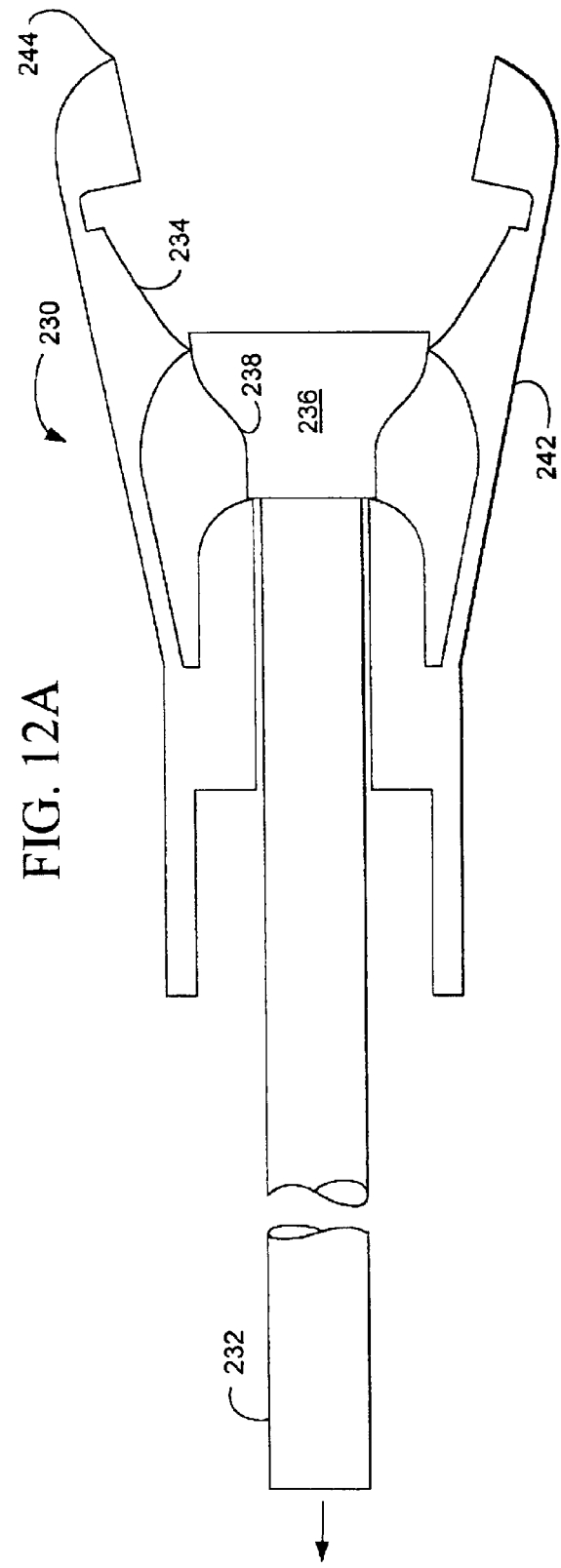
FIG. 12A
FIG. 12B

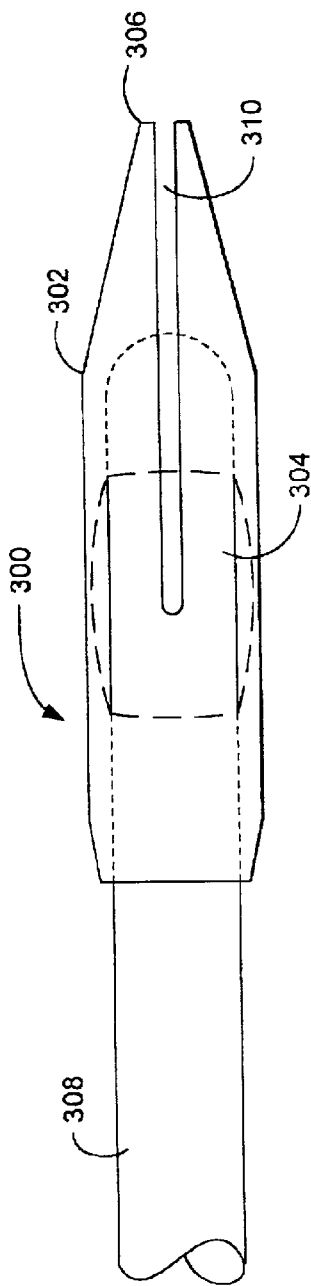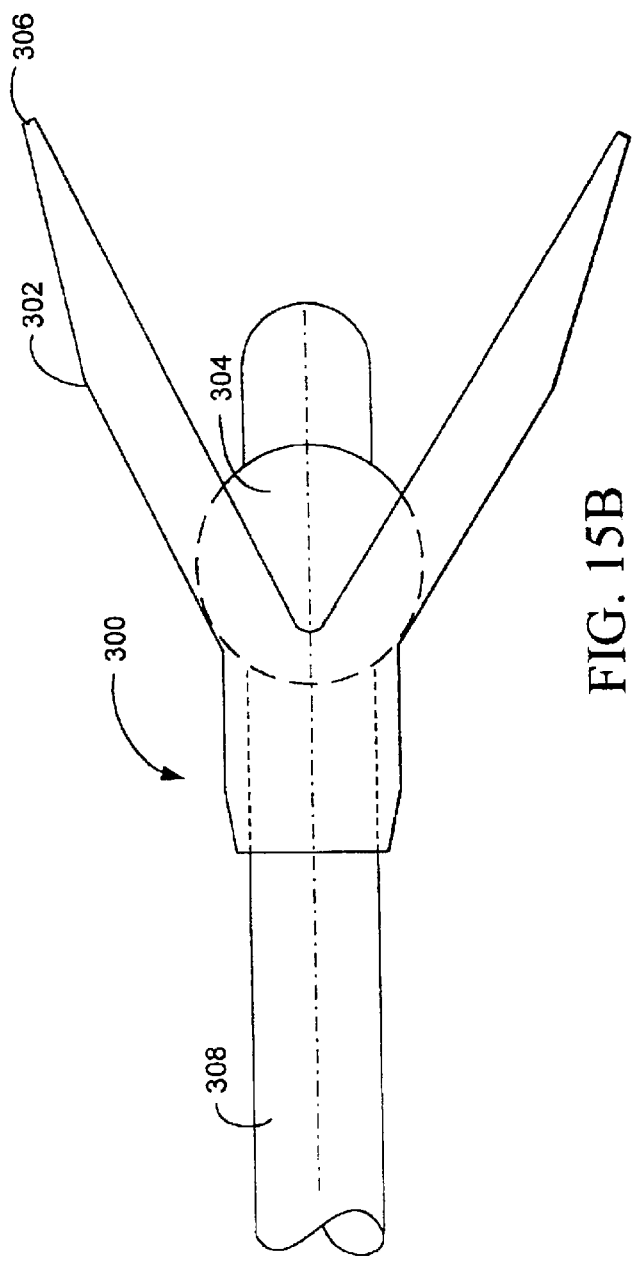
FIG. 15A
FIG. 15B

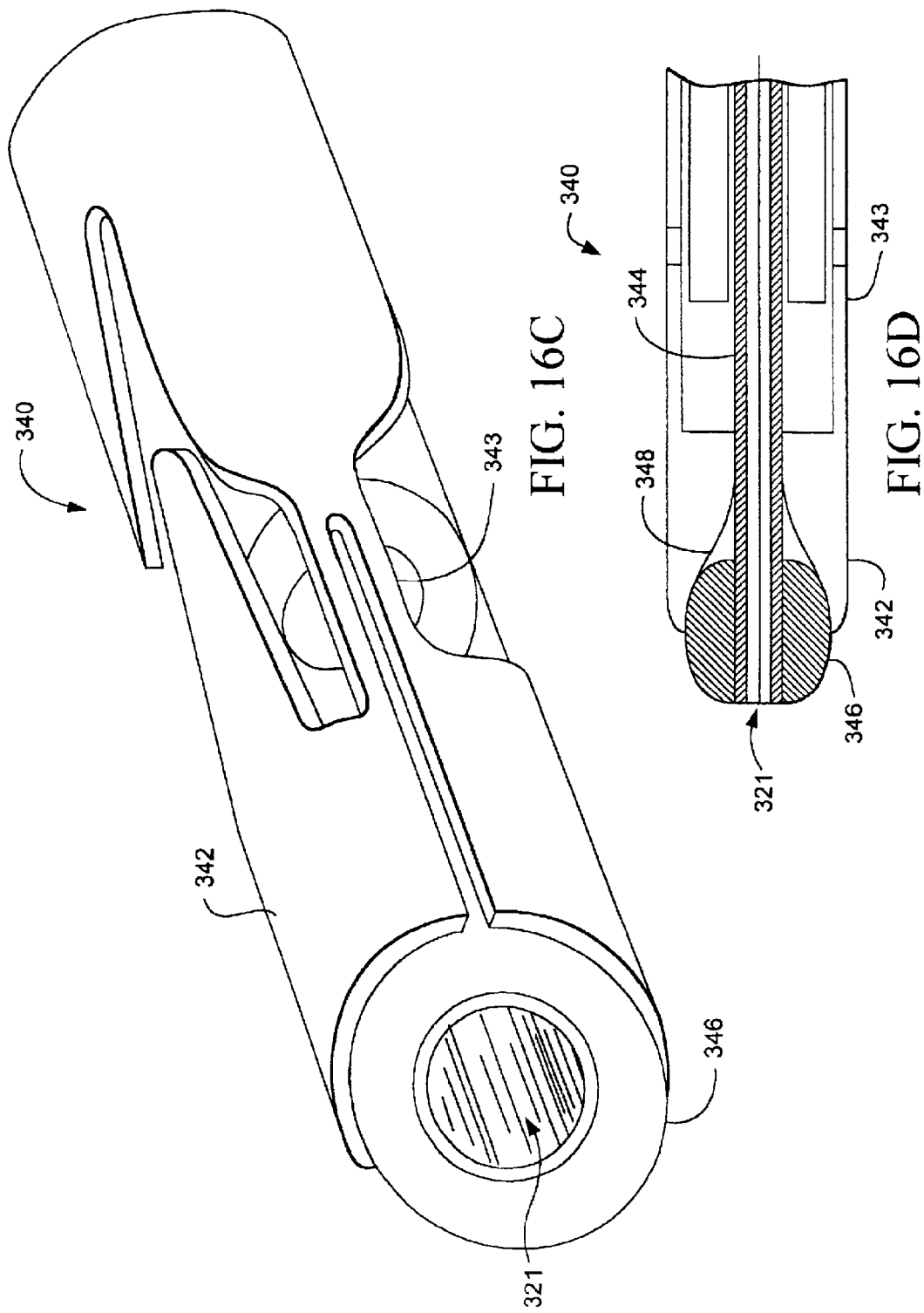

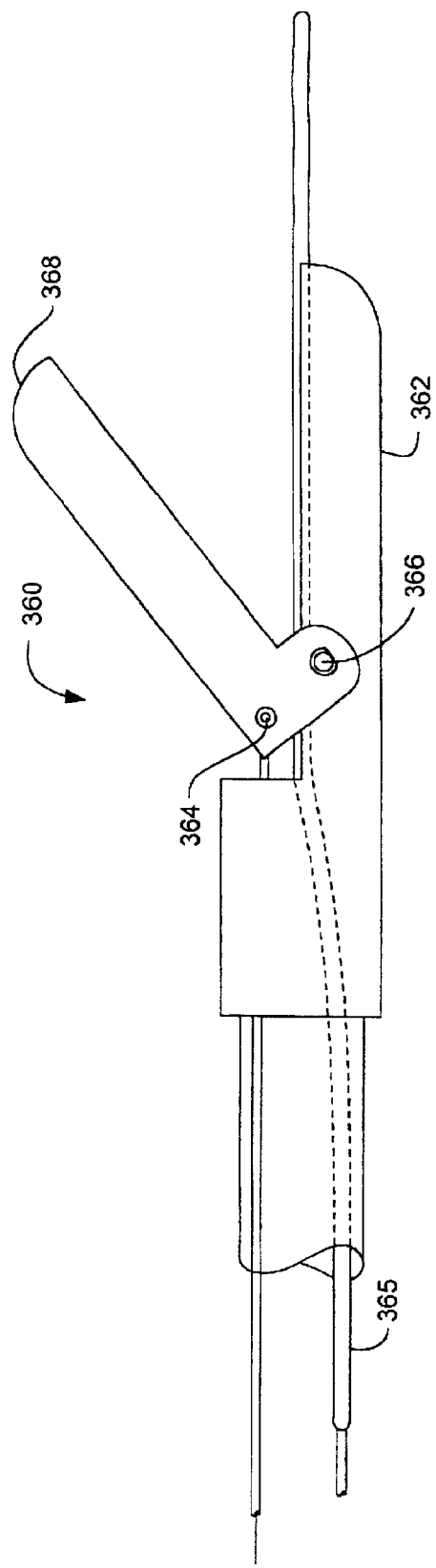
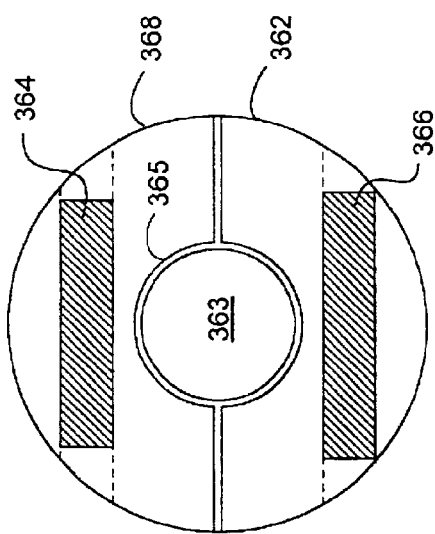
FIG. 18A
FIG. 18B

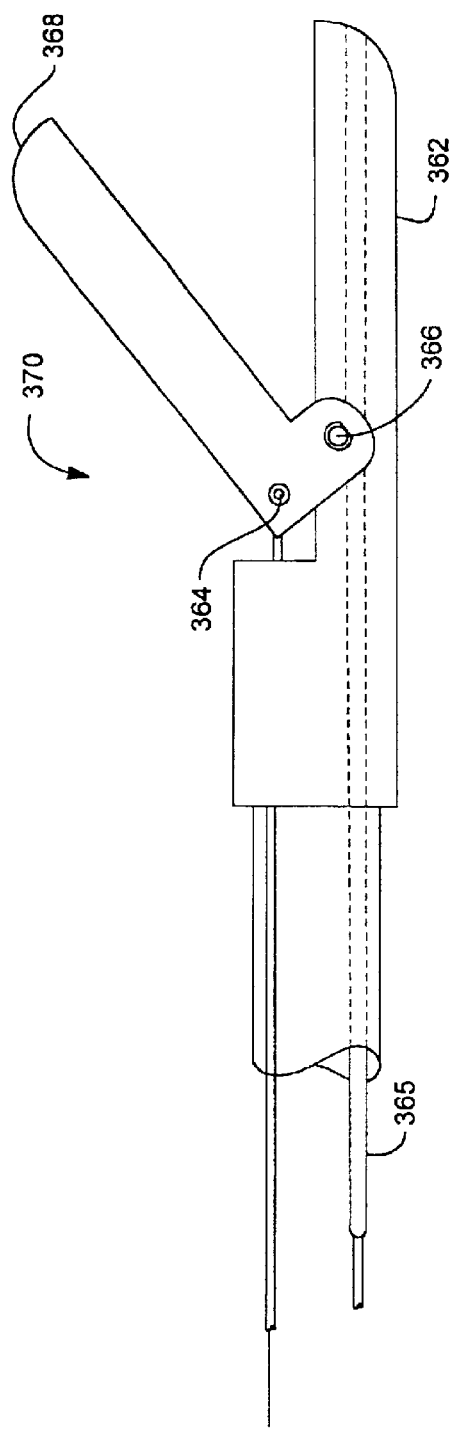
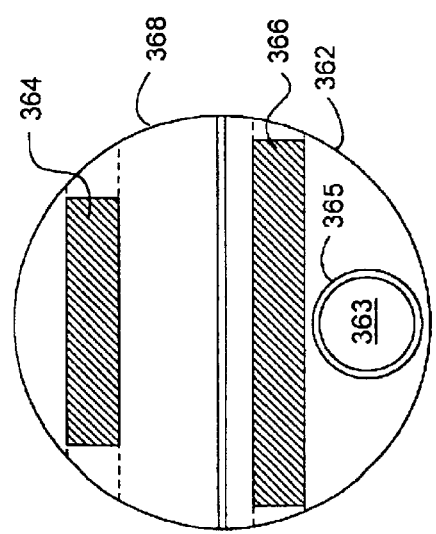
FIG. 18C
FIG. 18D intra-vascular catheter retracted leaving intra-coronary guiding catheter in position across occlusion

METHODS AND APPARATUS FOR TREATING VASCULAR OCCLUSIONS

This patent application is a continuation of U.S. patent application Ser. No. 09/149,874, filed Sept. 8, 1998 now U.S. Pat. No. 6,508,825, which is a continuation-in-part of U.S. patent application Ser. No. 08/775,264 filed Feb. 28, 1997 now U.S. Pat. No. 5,968,064.

FIELD OF THE INVENTION

The invention is generally directed to medical devices and catheters designed for the treatment vascular occlusions. More particularly, the invention is directed to cardiovascular catheters having the ability to sufficiently fracture, disrupt or displace a vascular occlusion in order to allow a guidewire to pass through the occlusion within the lumen of a blood vessel. The invention is further directed to a vascular catheter for crossing a substantially occluded blood vessel by disrupting the occlusion to provide a pathway that permits the passage of a guidewire or interventional cardiovascular device such as a stent or other catheter apparatus.

BACKGROUND OF THE INVENTION

Medical science has long sought effective treatments for disease states that cause stenosis (narrowing or obstruction) of the lumen (interior passage of the artery) of an artery. This condition, known generally as a vascular occlusion, is found in patients suffering from the disease of atherosclerosis (an accumulation of fibrous, fatty or calcified tissue in the arteries). Symptoms of arterial occlusion include hypertension (high blood pressure), ischemia (deficiency of circulation), angina (chest pain), myocardial infarction (heart attack), stroke, or death. An occlusion may be partial or total, may be soft and pliable or hard and calcified, and may be found at a great variety of sites in the arterial system including the aorta, coronary and peripheral arteries.

Of particular interest to cardiac medicine are the often disabling or fatal occlusions occurring in the coronary arteries (arteries supplying the heart). Traditionally, coronary artery occlusions have been treated by performing coronary bypass surgery. This is a procedure in which a segment of the patient's saphenous vein may be taken from the patient's leg and is grafted onto the affected artery at points proximal (upstream) and distal (downstream) to the occluded segment. While the procedure can improve the patients quality of life through reduced ischemia and angina, it is major surgical procedures with significant morbidity and mortality risks and a long convalesce period. Consequently, it is contraindicated for a significant portion of the patient population due to age and other factors. Moreover, in a significant percentage of patients, the saphenous vein graft may become occluded over the passage of time due to same disease processes which caused the original occlusion. If the patient has another saphenous vein, a second bypass procedure may be performed, once again incurring the risk, cost and prolonged hospitalization of this procedure. In fact up to 25% of bypass patients may require repeat surgery.

Newer, minimally invasive procedures are now preferred in the treatment of arterial occlusions. These procedures often include the use of long, thin, and highly flexible devices known in the art as catheters. During the procedure, the catheter is introduced into a major artery through a small arterial puncture made in the groin, upper arm, or neck, and is advanced and steered into the site of the stenosis: At the distal end of the catheter, various devices have been developed for operating upon the stenosed artery. For example, the more popular minimally invasive procedures include percutaneous transluminal coronary angioplasty (PTCA), directional coronary atherectomy (DCA), and stenting. PTCA employs a balloon to mechanically dilate the stenosis. In PTCA, a steerable guidewire is introduced and advanced under fluoroscopic observation into the narrowed artery and past the area of stenosis (e.g. blockage). Next, a balloon-tipped catheter is advanced over the guidewire until it is positioned across the stenosed segment. The balloon is then inflated, separating, fracturing or otherwise deforming the atheroma so as to enlarge the narrowed lumen of the artery sufficiently to increase blood flow to a previously ischemic or near ischemic section of the myocardium. Directional coronary atherectomy is another minimally invasive procedure that has been developed, a catheter containing a cutter housed in its distal end is advanced over the guidewire into the stenosed segment. The housing is urged against the atheroma by the inflation of a balloon, so that part of the atheroma intrudes through a window in the side of the housing. Under fluoroscopic observation, the cutter is used to shave away the atheroma. The shavings are collected in the nosecone of the housing and withdrawn along with the catheter. Similarly, stenting is another current procedure in which a wire framework, known as a stent, is compressed and delivered a balloon catheter. The stent is positioned across the stenosed segment of the artery. The balloon is inflated, dilating the stent and forcing the stent against the artery wall. The hoped-for outcome is that the stent will hold the arterial lumen open for a prolonged period. Frequently, a stent is placed in an artery immediately following PTCA or DCA. The catheters selected for many of the aforementioned procedures are known as "over-the-wire catheters." These catheters depend upon the positioning of a guidewire, which typically has a flexible portion at its distal end for steering. Over-the-wire catheters cannot be positioned adjacent the stenosis to carry out current procedures until the guidewire traverses or has been advanced across the stenosed arterial segment. Thus, where the occlusion is too severe to be crossed by a guidewire or where there is not enough room for the balloon, cutter, or stent delivery catheter, neither PTCA nor DCA nor stenting can be effectively performed.

Unfortunately, vascular occlusions often contain extremely hard, calcified tissue that forms an impenetrable barrier against the simple advancement of a guidewire across the occlusion. Even a less than total occlusion may contain complex structures which may trap or divert the steering end of the guidewire. Thus, the guidewire may not completely cross the occlusion, and may become diverted into the subintimal space between the atheroma and the arterial wall, or even become buried in the atheroma. In either case, the guidewire cannot be properly positioned across the stenosis to guide a balloon or cutting element. In such cases, bypass surgery may be necessary with the associated cost, risks, and recovery period. Thus, in patients suffering from severe or total arterial occlusion, it is preferable to do what has been difficult or impossible in the past, to open the severely or totally occluded artery itself, rather than by performing a bypass. If a guidewire and working catheter can be passed through or around the atheroma, the occlusion can be treated by a number of interventional procedures include PTCA, DCA, stenting, site-specific drug and radiation delivery or a combination of these different therapies.

Accordingly, it would be medically advantageous to circumvent a vascular occlusion. Appropriate devices and procedures for crossing the occlusion should be selected without perforating the blood vessel or artery being treated, an extremely serious and even life-threatening consequence. A physician will generally not use a system which would be unsafe, nor would patients want a physician to use such a system. Therefore, solutions to the problem of crossing a vascular occlusion such as an atheroma should be safe, and in many instances, include a system of guidance for the device to bypass such an occlusion. There has been a long felt need in the practice of interventional cardiology and radiology for a reliable guidance system for these types of vascular devices. As understood by those in the art, the device often travels through a complex, tortuous vascular anatomy before it even gets to the occlusion. Then the occlusion itself often has a irregularly shaped (e.g. eccentric) morphology. Attempting to cross such an occlusion without reliable imaging of the adjacent vasculature is dangerous. For example, it is easy to dissect the tissues of the arterial wall instead of the occlusion, thereby creating a false lumen and possibly perforating the artery. If enough blood from a perforated artery accumulates in the pericardial space surrounding the heart, it will result in a condition known as cardiac tamponade in which the heart is compressed and emergency surgical intervention is required to avert heart failure and death. Physicians have attempted to avoid such adverse events through the use of imaging systems/ procedures such as biplane fluoroscopy. This is an imaging system that has been used in conjunction with coronary catheterization wherein the physician observes two flat real-time x-ray images acquired from different angles. However, biplane fluoroscopy may be unreliable, costly, and relatively slow. Delay is unacceptable in many instances, for it contributes to trauma and stress and creates opportunities for complications and failures of technique. While advanced medical imaging systems may be of diagnostic interest, they are not a substitute for effective interventional treatment for severe occlusive arterial disease. There persists a long felt need in the art for a vascular device which is capable of successfully crossing an arterial occlusion with a relatively low risk of perforating the artery. What is especially needed is a therapeutic working device which assists the physician in safely restoring normal blood flow rates within diseased blood vessels. What is further needed is a vascular catheter system that may allow effective treatment of a severely occluded artery and, in particular, a totally occluded artery.

SUMMARY OF THE INVENTION

The present invention provides methods and apparatus for the treatment of vascular occlusions. It is an object of the invention to disrupt vascular occlusions or other blockages formed within blood vessels in order to provide pathways for the placement of guidewires, interventional devices and catheters as part of an overall effort to restore normal circulatory function. It is advantageous to cross a vascular occlusion by finding and/or creating a path with the least or relatively low mechanical resistance through or around the occlusion. The invention further provides apparatus and methods to tear or to mechanically fracture a vascular occlusion, or to separate a vascular occlusion from a blood vessel wall, with minimal risk of perforating the adventitia of an arterial wall.

One aspect of the invention provides apparatus for treating a vascular occlusion. A catheter may be selected comprising an elongated shaft that is formed with at least one lumen extending from the proximal section to the distal section of the shaft. A hinged spreading member may be positioned at the relatively distal section of the shaft. The spreading member may inclue a distal most end that moves in a substantially lateral direction away from the central axis of the shaft to disrupt a vascular occlusion. An actuating assembly may be also positioned along at least a portion of the elongated shaft to move or to direct the distal most end of the spreading member in response to an applied actuation force. The actuating assembly may further include a cam follower or other guiding region that is formed on a relatively interior portion of the hinged spreading member.

Another embodiment of the invention includes an intravascular catheter for expanding or stretching vascular tissue. The intravascular tissue expanding catheter may include a catheter shaft defined by a distal end having at least one conduit extending along the longitudinal axis of the catheter shaft. A housing may be formed at the distal end of the catheter shaft wherein the housing includes at least one hinged deflecting member defined by a distal most tip that moves in a substantially lateral direction away from the central axis of the shaft to expand tissue surrounding a vascular occlusion. An actuation assembly may be also positioned along the catheter shaft to move the distal most tip of the hinged deflecting member away from the central axis of the shaft. The catheter shaft may be also formed of braided material and a flexible inner coil shaft component that supports a column load.

It is a further object of the invention to provide a vascular catheter that is formed with a tissue expansion assembly for tearing or fracturing an occlusion within a blood vessel. The vascular catheter may comprise a catheter body formed with a distal section and at least one longitudinal conduit. At least one tissue expanding member may be connected to the distal section of the catheter body. The expanding member may include a relatively proximal portion and a relatively distal portion wherein the distal portion is configured to spread apart relative to the proximal portion of the expanding member. An actuation assembly may be positioned within the catheter body, and may be in communication with the proximal portion of the tissue expanding member to spread apart the distal portion of the expanding member. The distal section of the catheter may further include a relatively fixed extension. The relatively proximal portion of the tissue expanding member may be connected to the fixed extension with a hinge pin to permit the relatively distal portion of the tissue spreading member to move away from the fixed extension.

It is an additional object of this invention to provide flexible catheter shafts that support variable column loads. The shaft may comprise an outer catheter shaft defined by a longitudinal shaft lumen. An inner coiled body that is defined by a longitudinal coiled lumen may be positioned within the longitudinal shaft lumen for column load reinforcement of the outer shaft. A movable pulling element may be slidably positioned within the longitudinal coiled lumen for relative movement of the pulling element with respect to the inner coiled body. Another variation of the invention is to provide a catheter shaft with a reinforced outer catheter shaft. An outer shaft may be formed with a lumen that includes an inner shaft positioned within the outer shaft lumen. The inner shaft may further include an actuation lumen and at least one inner shaft lumen, and may be formed by extrusion. A column load reinforcement sleeve may be formed with a sleeve lumen that is positioned within the actuation lumen. In addition, an actuation wire may be slidably positioned within the sleeve lumen to provide relative movement of the wire within the sleeve. At least one inner shaft lumen may be also configured for placement of a guidewire. In yet another variation, a reinforced catheter body may be selected having a braid reinforced catheter shaft formed with a longitudinal catheter shaft lumen. An actuation conduit and a guidewire conduit may be separately formed within the longitudinal lumen of the catheter shaft. Additionally, a compression or wound coil that provides compression support may include a coil lumen and may be positioned within the actuation conduit for column load reinforcement of the actuation conduit. A pulling element may be positioned within the coil lumen for relatively slidable movement within the coil.

Another object of the invention is to provide an intravascular catheter for expanding tissue that includes a catheter body formed with an outer reinforced shaft coaxially formed about an inner coiled body for column load reinforcement of the catheter body. The inner coiled body may further include an actuation conduit leading to a relatively distal section of the catheter body. A tissue expanding member may be connected to the distal section of the catheter body. The interior surface of the tissue expanding member may include a cam follower. Additionally, the expanding member may be defined by a relatively proximal portion and a relatively distal portion so that the distal portion is configured to expand relative to the proximal portion of the expanding member. An actuation element may be selected and positioned within the actuation conduit formed in the inner coiled body. The actuation element may be formed as a wire or tube that supports actuation forces, and may further include a cam for communication with the interior cam follower of the tissue expanding member to expand the distal portion of the expanding member when actuated. The surface of the cam includes a variety of curved or non-linear configurations, and is preferably complementary to the shape of the corresponding cam follower.

Another aspect of the invention includes methods for disrupting and crossing a vascular occlusion. The vascular occlusion may be separated, fractured or displaced to provide a pathway across the obstruction in order to accommodate the placement of a guidewire or interventional device as part of an overall effort to restore normal circulatory function within the blood vessel.

It is an object of the invention to provide methods of displacing a vascular occlusion by initially selecting a vascular catheter that is formed with a spreading member positioned at the distal region of the catheter. The spreading member may be configured to spread or stretch apart an occlusion and/or vascular tissue, and may be activated or actuated in response to a directed force along the longitudinal axis of the catheter. An actuator assembly may be positioned along at least a portion of the catheter to transmit the directed force which may be applied linearly or rotationally, or by transmitting pressure relatively distally to an actuation balloon, from a remote or proximal portion of the catheter to the spreading member. The vascular catheter may be positioned adjacent to a substantial or total vascular occlusion within a selected blood vessel before applying a directed force to the actuator in order to deploy or to spread apart the spreading member. The occlusion may be displaced or disrupted based upon the different elastic properties between stretchable blood vessel walls and materials which form vascular occlusions. The vascular occlusion itself may be also fractured or otherwise disrupted to provide a passageway across the occlusion in order to accommodate the placement of a guidewire or interventional device such as a stent after removing the vascular catheter from the selected blood vessel. The spreading member may be spread apart to disrupt a vascular occlusion to create a path substantially through or around at least a portion of the occlusion. Additionally, the spreading member may stretch out the blood vessel wall creating a path substantially between the occlusion and the blood vessel wall. When the vascular occlusion is adhered to the wall of a selected blood vessel, the spreading member may be also expanded or spread apart to separate the layers of the blood vessel wall. The vascular catheter may be distally advanced through the vascular occlusion to pass through at least a portion of or entirely through the occlusion. Another variation of the invention includes the method of selecting a guidewire and passing the guidewire through a conduit formed in the vascular catheter. The guidewire may extend along to the length of the catheter and reach the site of an occlusion. Upon activation of at least one spreading member, the guidewire may be advanced through or around at least a portion of the occlusion.

Other various methods of crossing a substantially occluded blood vessel are provided herein in accordance with the concepts of the invention. An intravascular catheter may be selected that includes a distally mounted tissue expanding member defined by a relatively proximal portion and a relatively distal portion so that the distal portion is configured to expand relative to the proximal portion of the expanding member. In addition, an actuation assembly may be positioned within the intravascular catheter to transmit a spreading force in order to expand the distal portion of the expanding member. The tissue expanding member may be placed or positioned within a blood vessel in proximity to an occlusion, and subsequently activated to stretch the blood vessel wall and disrupt the occlusion to permit the passage therethrough. The tissue expanding member may be deactivated thereafter, and the intravascular catheter removed from the target blood vessel. A guidewire may be positioned within the passageway formed within or alongside the disrupted or displaced occlusion in order to facilitate the placement of a stent or other interventional device. The guidewire may also pass through at least a portion of the occlusion before the tissue expanding member is deactivated. The catheter may be similarly advanced through or across at least a portion of the occlusion upon disruption of the vascular obstruction.

In yet another variation of the invention, a method is provided for crossing a coronary vascular occlusion. This procedure may begin by selecting and advancing a guidewire within a blood vessel to a vascular occlusion. An intra-coronary guiding catheter may be advanced over the guidewire so that the distal end of the catheter is in proximity to the vascular occlusion. The guidewire may be thereafter removed from the blood vessel. An intravascular catheter may be selected for placement within the guiding catheter that includes a spreading member positioned that is responsive to directed force along its longitudinal axis. Additionally, an actuator assembly may be positioned along the intravascular catheter to transmit a directed force applied from the proximal portion of the catheter to the spreading member. The intravascular catheter may be advanced through the intra-coronary guiding catheter to position the spreading member of the intravascular catheter substantially adjacent to the vascular occlusion within the blood vessel. A directed force may be applied to the actuator assembly to spread apart the spreading member in order to displace the vascular occlusion. Another variation of this method may include the advancement of the intra-coronary guiding catheter past or across the occlusion before removing the intravascular catheter from the blood vessel. In addition, a guidewire may be advanced past or across the displaced vascular occlusion after removing the intravascular catheter and before removing the intra-coronary guiding catheter.

Other variations of the invention described herein include a vascular catheter formed with a blunt end assembly for tearing or fracturing an occlusion within a blood vessel. It is an additional object of this invention to provide such an assembly wherein the assembly includes a catheter having a distal end and a proximal end and wherein a working end member fits in an interchangeable manner to the distal end of the catheter and wherein the working end comprises a blunt end member in accordance with the invention. It is an additional object of this invention to provide such an assembly wherein the blunt end member has a first closed position and a second open position and may be repeatedly opened and closed for tearing/fracturing the occlusion within the lumen of the blood vessel. It is a further advantage of the invention to provide a tearing or fracturing force that is stably applicable to a severe or total arterial occlusion. A mechanical working element may be stably operable upon a severe or total arterial occlusion in a manner unlikely to perforate the adventitia or other layers of the arterial wall. In addition, the blunt end member assembly may comprise: a blunt end member connectable to the distal end of the catheter, the blunt end member sized and shaped for fitting within the blood vessel and for tearing and/or fracturing the occlusion, the blunt end member having a first position for allowing the blunt end member to be located at the occlusion and a second position for fracturing the occlusion; and an actuation member for moving the blunt end member between the first and second positions, whereby the blunt end member is connectable to the distal end of the catheter and the blunt end member is deliverable to the occlusion in the first position and is actuable to a second position for fracturing the occlusion.

In one embodiment of the invention, an over-the-wire vascular catheter is provided comprising a blunt end member disposed at the distal end thereof and a securing balloon disposed about the distal end zone of the catheter proximal to the blunt end member. The catheter and blunt end member may be sized and shaped so as to allow the blunt end member to be advanced into contact with an occlusion in an artery. The balloon may be disposed on the outer surface of the distal end zone of the catheter and is inflatable to secure the distal end of the catheter within the artery, and thus to maintain engagement or longitudinal registration of the blunt end member with the occlusion. A balloon inflation lumen may be provided in the catheter. The blunt end member may comprise four jaw sections flexibly attached to the distal end of the catheter, and may be arranged symmetrically about the longitudinal axis thereof. The catheter may comprise a retractable actuation shaft having a ball-shaped ferrule fixed to the distal end thereof between the jaw sections. To accommodate a guidewire, the actuation shaft may include a lumen and the ferrule includes a center opening. The jaw sections may have a first, closed position in which the catheter may be advanced to engage the jaws with the occlusion. When the actuation shaft is retracted, the ferrule or cam impinges upon the inner surfaces or cam followers of the jaw sections, urging them apart toward a second, open position to fracture the occlusion. The ferrule may be formed with a frusto-conical profile.

In another embodiment of the invention, each jaw section may include a rectangular distal end or a spade-shaped configuration. In the first, closed position, the jaw sections form a channel substantially confining the guidewire to the longitudinal axis of the blunt end member. It is an advantage of this embodiment that when the jaw sections are in the first, closed position, a guidewire may be advanced into a portion of the occlusion bounded by the points of contact with the distal ends of the jaw sections. In another embodiment of the invention, the jaw sections may be fabricated from an alloy comprising nickel and titanium. It is an advantage of this exemplary embodiment of the invention that the superelastic properties of the alloy facilitate closing of the jaw sections when the ferrule is deactivated or de-actuated by an actuation member.

In another exemplary embodiment of the invention, the actuation member includes an actuation cable disposed in the catheter. The proximal end of the cable is manipulable from the proximal end of the catheter and the distal end of the cable is attached to the ferrule. It is an advantage of this exemplary embodiment of the invention that the cable increases the tension capacity of the actuation member during retraction of the ferrule. A part of the lumen of the actuating member may include a friction reducing coating. It is an advantage of this embodiment of the invention that the catheter slide easily over the guidewire. In another embodiment of the invention, the mating surface defined by the impingement of the actuation member upon the blunt end member includes a friction reducing coating. It is an advantage of this exemplary embodiment of the invention that the actuation member encounters minimal frictional resistance while urging the jaw sections apart.

In another embodiment of the invention, the entire blunt end member may be fabricated from a single piece of material. It is an advantage of this exemplary embodiment of the invention that fabrication of the blunt end member does not require attachment or assembly of multiple parts.

Another embodiment of the invention provides a blunt end member that includes a rigid tubular reinforcing member slidably disposed about the actuation shaft inside the distal end zone of the catheter. A tubular support member is disposed on the outer surface of the distal end of the catheter. The distal end of the support member includes a spring member deformably supporting a plurality of jaw sections. The support member may be crimped onto the distal end zone of the catheter, securing the catheter onto the reinforcing member. It is an advantage of this embodiment of the invention that a simple yet secure attachment is formed between the catheter and the blunt end member.

These and other objects and advantages of the invention will become more apparent upon further consideration of the specification and drawings. For further understanding of the objects and advantages of the invention, reference may be made to the following description in conjunction with some of the accompanying drawings in which similar components are identified with similar reference numerals.

BRIEF DESCRIPTION OF THE DRAWINGS

FIG. 1 is a perspective view illustrating occlusion treatment apparatus positioned within an occluded blood vessel.

FIG. 2 is a side view of a catheter having tissue expansion members similarly shown in FIG. 1 that are in the process of fracturing or tearing a total occlusion.

FIGS. 12A–B are cross-sectional views of a vascular tissue expansion and actuation assembly formed with deflecting members shown in an closed and open position.

FIGS. 15A–B are side views of distal mounted spreading members with an actuating balloon that spreads open the distal end portions of the spreading members.

FIGS. 16A–D illustrate various distally mounted deflecting member assemblies formed with a plurality of deflecting members.

FIGS. 18A–D are simplified views of a hinged deflecting member and positioning with a guidewire.

DETAILED DESCRIPTION OF THE INVENTION

Figures 3, 4:
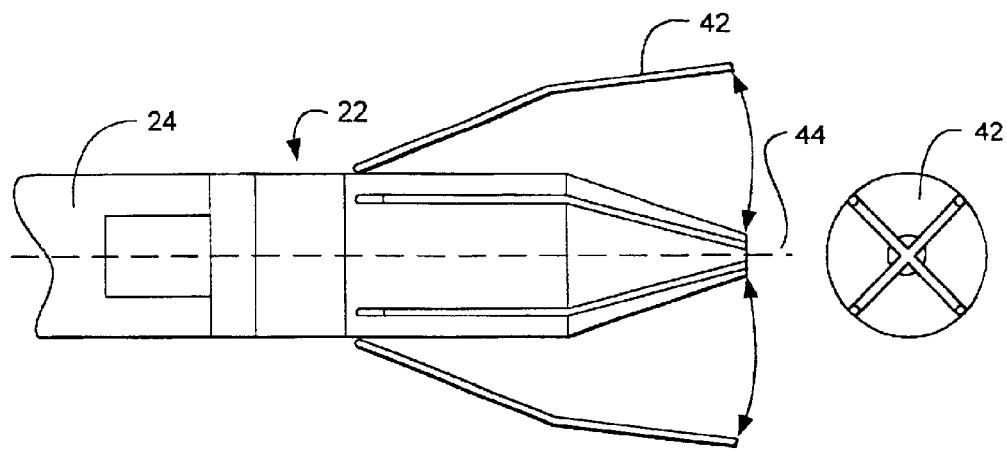
FIG. 3 is an enlarged side view of tissue expansion or blunt end members having a first closed position and a second open position.
FIG. 4 is an end view of tissue expansion members illustrated in FIG. 3 that are shown in a closed position.

The present invention provides methods and apparatus for disrupting and crossing a vascular occlusion. Each of the disclosed embodiments may be considered individually or in combination with other variations and aspects of the invention. While some variations of the invention illustrated herein may seem particularly directed to coronary artery applications and bypass grafts, the drawings are illustrative only, and it should be understood that the invention is similarly applicable to any blood vessel that may become obstructed due to various conditions including vascular disease.

FIGS. 1 and 2 generally provide illustrations of an intravascular catheter formed in accordance with the principles of the present invention. The catheter may be used to disrupt an occlusion formed within various sections of arterial or venous blood vessels. The catheter may include a housing or blunt end member assembly formed with a relatively proximal portion attached to a distal end of an elongated catheter shaft by applying adhesive, crimping or other joining techniques. The housing may be further defined by a relatively distal portion that is configured for intimate contact or communication with an occlusion and/or a blood vessel wall. The distal mounted housing may further include one or more hinged spreading or deflecting members that may be mechanically activated by an actuating member such as a pull wire or tube. A spreading or mechanical force may be thus applied to the blood vessel wall and occlusion so as to tear, fracture or otherwise disrupt, the occlusion adjoining the vessel wall. This disruption of the occlusion may create a channel or a passageway of sufficient size for the passage of a guidewire or therapeutic catheter around or through at least a portion the obstruction as part of an overall effort to restore regular circulatory function surrounding the occluded vascular region.

With particular reference to FIG. 1, there is shown a blunt end member assembly formed in accordance with this invention, generally designated by the numeral 20. The assembly 20 may include a blunt end member 22 and a catheter 24. An actuation member indicated by dotted lines 26 may move or actuate the blunt end member from a first closed position, as illustrated in FIG. 1, to a second open position, as illustrated in FIG. 2. The catheter may be initially positioned using a guidewire 28 so that the extreme distal end of the blunt end member 22 may be adjacent to a substantial or total occlusion. Once positioned, the catheter 24 may remain relatively fixed at a particular location with a member for stabilizing the assembly 20 in a blood vessel, namely, a balloon member 30. The balloon member 30 may be inflated as shown in FIG. 2 so that the catheter 24 remains in place during actuation of the blunt end member 22.

As illustrated in FIGS. 1 and 2, the blunt end member 22 may be positioned at various blood vessel junctures including a location adjacent to a total occlusion where a bypass is in the process of failing. The bypass may develop diffuse stenosis as shown in FIGS. 1 and 2. Consistent with the above description, it is quite likely that where stenosis has developed sufficiently to block an arterial blood vessel, after a bypass is performed, stenosis in the bypass will also occur or accumulate even to a point where the bypass may be also blocked or become totally occluded. Using a blunt end member 22 formed in accordance with the invention, the original, native blood vessel may be re-opened which allows the bypass to fade as the primary source of blood flow. It should be noted that different aspects of the invention illustrated herein describe methods and apparatus directed particularly to native coronary arteries. However, it will be of course appreciated that the drawings are illustrative only, and that the invention may be applied to any situation where a blood vessel, such as a coronary artery, has been occluded by stenosis or vascular disease. Among other features provided herein, the invention disrupts or fractures occlusions to allow a native artery or blood vessel to resume its primary responsibility of supporting blood flow.

Figure 5:
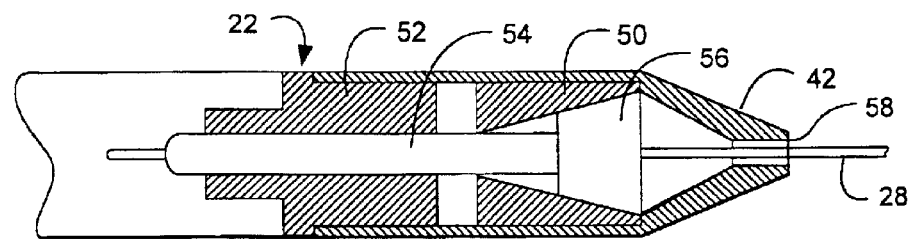
FIG. 5 is a cross-sectional view of hinged spreading members shown in a relatively closed position.

FIGS. 3–6 provide further illustrations of a blunt end member 22 having various open and closed positions. The blunt end member 22 may be formed with a proximal end attached to the distal end of a catheter 24. The methods of attachment for the blunt end member 22 include conventional techniques within the skill and knowledge of those skilled in the art. The blunt end member 22 may include a set of sectional members defining the jaw sections 42. The jaw sections 42 may be located at the distal end of the blunt end member 22, and may be spaced apart at equal distances relative to a longitudinal center line 44 shown in FIG. 3. The jaw sections 42 may be opened to a second position shown particularly in FIGS. 3 and 6, and may be closed or returned to a first position as shown in FIGS. 3–5. An actuation wire or actuation member 54 may be provided within the assembly to move the jaw sections 42 from its first closed position to its second open position. In various embodiments, the jaw sections 42 may have a variety of geometries, including but not limited to, spade shaped, straight with a concave curve at the end, straight with convex curve at the end, triangular (needle nose), rectangular and combinations thereof. The jaws 42 may be spaced apart or separated from one another even when closed as shown in FIG. 4. This configuration may allow the jaw sections 42 to meet relatively flush against an arterial wall and an occlusion for optimal fracturing or disruption of the occlusion.

Figure 6:
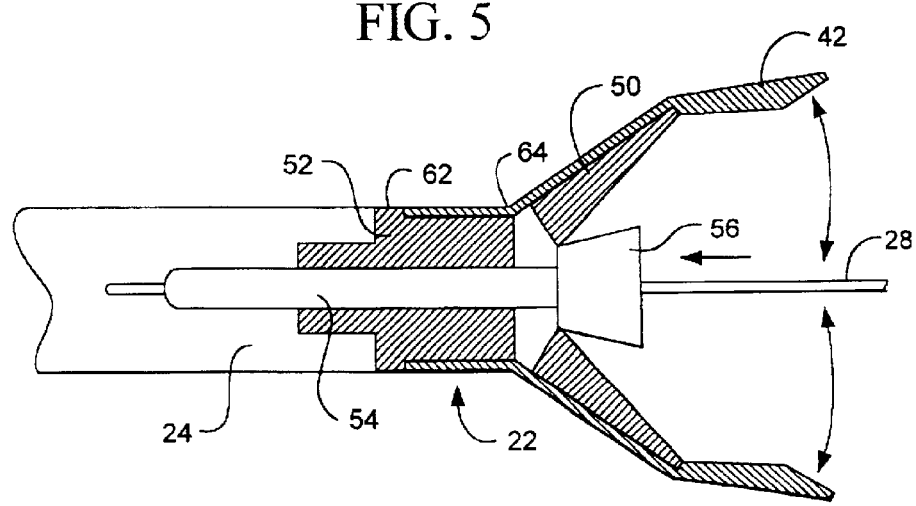
FIG. 6 is a cross-sectional view of hinged spreading members similarly illustrated in FIG. 5 that are shown in a relatively open position.

With respect to FIGS. 5 and 6, there is shown an assembly view of another the blunt end member 22 formed in accordance with the invention. The blunt end member 22 may include a reverse conical urging member 50 and a spaced apart support member 52. The members 50 and 52 may be sized and shaped to fit within the same cavity or lumen of a catheter 24. Each of the members 50 and 52 may include a center opening along a longitudinal center line of the assembly. The openings of members 50 and 52 may be aligned so that a guidewire tube 54 may be positioned in the openings to slide toward and away from the proximal end of the catheter 24. A ferrule 56 may be attached to or bonded together with the guidewire tube 54 as shown in FIGS. 5 and 6. The bonding techniques used may be similar to those for joining the catheter 24 and the blunt end member 22. Additionally, bonding may be done by use of adhesives such as cyanoacrylate, soldering, or chemical or physical bonding, of a suitable kind. The guidewire tube or actuation member 54 being thus, permanently connected to the ferrule 56 in a bond which is strong enough to withstand the urging forces exerted against an occlusion. The ferrule 56 may also have a center opening aligned with the center openings of the members of 50 and 52. However, the center opening of the ferrule 56 may be formed with a relatively smaller diameter to match the dimensions of an inner guidewire 28 as opposed to the relatively outer guidewire tube 54. Alternatively, the ferrule 56 may be designed to accommodate only the guidewire 28 and not the guidewire tube 54. The guidewire 28 may be inserted in the center opening of the ferrule 56. The ferrule 56 may be defined by a frusto-conical shape, while the urging member 50 forms a reverse compatible shape for sliding against the frusto conical shape of the ferrule 56. The surfaces where each of the ferrule 56 and the urging member 50 contact, define a mating surface. The materials selected for each of the ferrules 56 and urging member 50 may be compatible for such mating sliding contact. In response to actuation, the ferrule 56 may be pulled toward the proximal end of the catheter 24 causing the ferrule 56 to slide against the urging member 50 so that the mating surfaces of each sliding across one another. As the ferrule is pulled towards the proximal end of the catheter, an increasing force is urged against the jaw sections 42 for spreading apart the jaw sections 42. Upon full activation of the actuation member the jaws may be fully opened as generally shown in FIG. 6. It will also be appreciated that the jaw sections 42 may be also spaced apart a sufficient distance when closed along the longitudinal center line 44 so a guidewire may be guided thereby as shown in FIGS. 3–5. The jaw sections 42, when closed, may form an internal guide 58 for sliding the guidewire toward and away from the distal end of the catheter 24. The interior opening of the members 50 and 52 may also provide a guide for the guidewire tube 54 as the jaw sections 42 are opened and closed in repeated use. It may be advantageous to coat the interior opening of the members 50 and 52, as well as the exterior of the guidewire tube 54, with Teflon® or a similar polymer so that the friction from the movement of sliding through the internal opening is greatly reduced. A reduction in friction may result in more force being effectively applied by the ferrule 56 against the urging member 50 which may maximize the amount of tearing or fracturing force applied by the blunt end member 42 to the arterial wall. The guidewire tube 54 may be a braided strand, and thus can be quite abrasive to the internal opening of the members of 50 and 52. Thus, the application of a friction-reducing coating to guidewire tube 54 or member 50 and 52 may be particularly appropriate to reduce the friction in the sliding movement. The guidewire tube 54 may be also a nitinol hypotube. Additionally, the mating surfaces of the urging member 50 and the ferrule 56 may be as smooth as possible, and may be chosen from compatible materials which minimize the amount of friction developed as the mating surfaces slide against one another in an effort to fracture an occlusion. In various embodiments, the urging member 50 may be made from nickel titanium alloy and the ferrule 56 may be constructed from stainless steel. Again, the mating surfaces of the ferrule 56 and urging member 50 may be formed as smooth as possible to minimize the friction therebetween.

As shown in FIGS. 5 and 6, the support member 52 may provide support both internal and external to the assembly. The support member 52 may remain fixedly attached to the distal end of the catheter 24, and may provide an internal opening for the sliding movement of the guidewire tube 54. Additionally, the jaw sections 42 have a proximal end zone which may surround both the urging member 50 and the support member 52. The proximal end zone of the jaw sections 42 may secure the members 50 and 52 together to provide the assembly. As shown in FIG. 6, the support member 52 may be notched to form a shoulder 62 that provides a secure connection fit with the jaw sections 42. In another exemplary embodiment in accordance with a unified assembly, the jaw sections 42 may be notched with an opening at elbow 64 as shown in FIG. 6. This configuration may allow space for deformation of the jaw sections 42 along an axis predetermined by the angle and length of the opening. It should be understood that the blunt end jaw members 42 may be formed of various materials with sufficient strength to withstand the mechanical forces necessary to fracture, tear or dislodge a vascular occlusion. In a preferable embodiment, the jaw sections may be made from nickel titanium that is both biocompatible and has sufficient strength for the function intended herein. It will of course be appreciated that the entire assembly, including members 50 and 52, as well as the jaw sections 42, may be formed from a single piece of nickel titanium to provide a unified assembly. Different components of the described assemblies may be made from a variety of materials including stainless steel, nickel titanium or other shape memory alloys and engineering plastics known to those skilled in the art. Additionally, other polymers or metal materials, which are also bio-compatible and have the mechanical characteristics necessary to perform the functions herein, are equally suitable.

Figure 7:
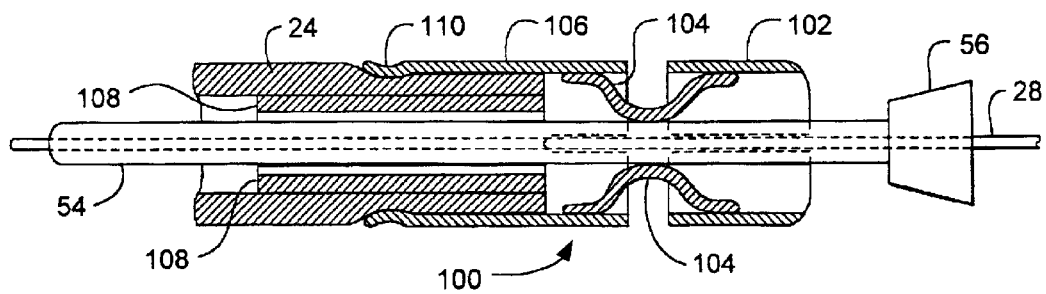
FIG. 7 is a cross-sectional view of hinged deflecting members in accordance with the invention that are shown in a closed position.
Figure 8:
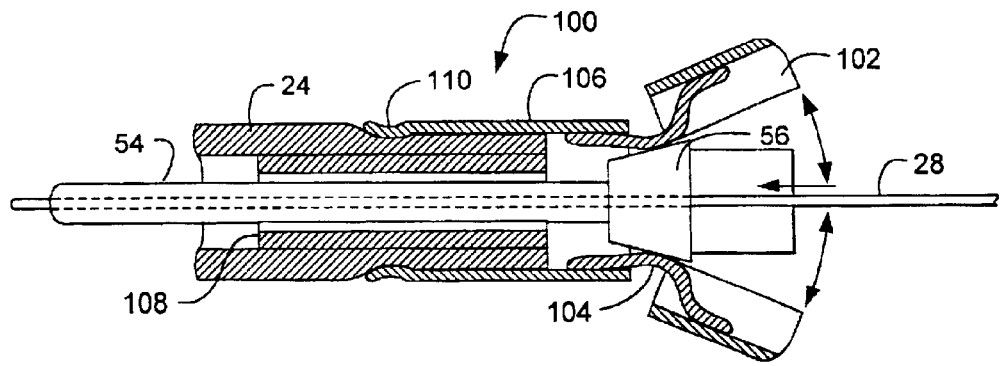
FIG. 8 is a cross-sectional view of the hinged deflecting members similarly shown in FIG. 7 that are shown in an open position.
Figures 9, 10:
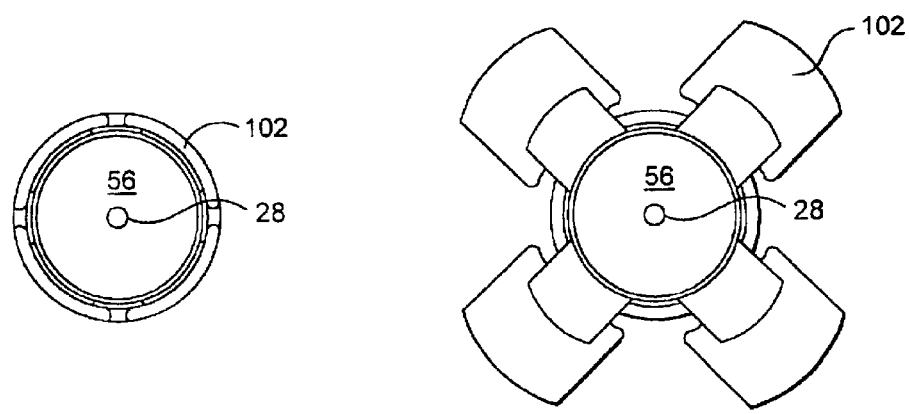
FIG. 9 is an end view of the deflecting members illustrated in FIG. 7 shown in a relatively closed position.
FIG. 10 is an end view of the deflecting members illustrated in FIG. 8 shown in a relatively open position.

FIGS. 7–10 illustrate yet another embodiment of a blunt end member 100 formed in accordance with this invention. The blunt end member 100 may include one or more jaw sections 102. A reinforcing member 108 may be positioned between a catheter tube 24 as shown in FIGS. 7–8, and a guidewire tube 54 may be placed in the guidewire lumen of the catheter tube. A ferrule 56 may be attached to the guidewire tube 54 as discussed previously with regard to the other described embodiments of the invention. The blunt end member 100 may also include a spring or hinge member 104 and a support member 106. The spring member 104 maybe formed with a mating surface for mating with the ferrule 56. Upon actuation, the ferrule 56 may be pulled toward the proximal end of the catheter 24, and the mating surfaces may engage and separate the jaw sections 102 to an open position as shown in FIGS. 8 and 10. Upon releasing the actuation member, the spring member 104 may urge the jaw sections 102 back to their original or closed positioned as shown in FIGS. 7 and 9. The spring member 104 may serve to connect the jaw sections 102 and the rest of the blunt end member 100, more specifically, the support member 106. The support member 106 may be crimped at its proximal end 110. The reinforcing member 108 may be positioned so that the crimp in the support member 106 sandwiches the distal end of the catheter tube 24. It will be appreciated that the hoop strength provided by the reinforcing member 108 may enable a secure attachment of the support member to the distal end of the catheter tube 24. It will be further appreciated that the crimp in the support member, plus the added hoop strength provided by the reinforcing member 108, may provide a secure connection for the entire blunt end member 100. Typically, the blunt end member 22 may be supported by the connections at the joining of the spring 104, the jaw sections 102, and support member 106. These joints can be formed in a variety of ways using adhesive bonding and metal joining methods well known in the art. For example, it may be preferable to bond the members with an epoxy, should they be made of a polymer, or to use welding, soldering, or brazing if the members are made from metal. In a preferable exemplary embodiment, the spring 104, the support member 106 and the jaw sections 10 may be formed from the same material such as nickel titanium. However, other combinations of materials such as spring steel and the like are also suitable. In other embodiments, it is also contemplated within the scope of the invention to form the support and spring members, 106 and 104, respectively, from stainless steel. Additionally, the reinforcing member 108 may be made alternately from nickel titanium or stainless steel. It is also contemplated that various other types of materials are suitable for manufacturing of the blunt end member 100 such as stainless steel and high strength medical plastics such as polycarbonate.

Another aspect of the invention is directed to methods of disrupting a vascular occlusion with apparatus similarly shown in FIGS. 7–10. As shown in FIG. 7, the blunt end member 100 may be placed in a first closed position. As is typical in interventional procedures, a guidewire 28 is fed through the lumen of the blood vessels of a patient. Upon reaching the selected location, the guidewire will meet an occlusion. The blunt end member 100 with the ferrule 56 will be positioned, as described earlier, directly adjacent to the occlusion. Although not shown, it will be appreciated that positioning balloons 30 may also be adapted for use with any of the embodiments shown in FIGS. 7–10. After stabilization or positioning of the catheter 24 in the lumen of the blood vessel, the blunt end member 100 may be activated by pulling on an actuation member 26 such that the mating surfaces of spring 104 and the ferrule 56 are brought into contact with one another. The ferrule 56 may move the jaw sections 102 away from the longitudinal center line of the catheter. This operation may be repeated until the occlusion is fractured or broken apart, or until the occlusion is sufficiently separated from the inner the blood vessel wall to permit the passage of an interventional device as described herein. As a result, the guidewire 28 may be advanced through the natural lumen of the blood vessel. The catheter 24 may be subsequently removed, and another interventional device may be positioned at or near the vicinity of the occlusion. Such interventional devices may include an angioplasty or atherectomy device, or a stent or other known interventional devices and methods, for treating the occlusion once the guidewire 28 is positioned across the occlusion.

Figure 11A:
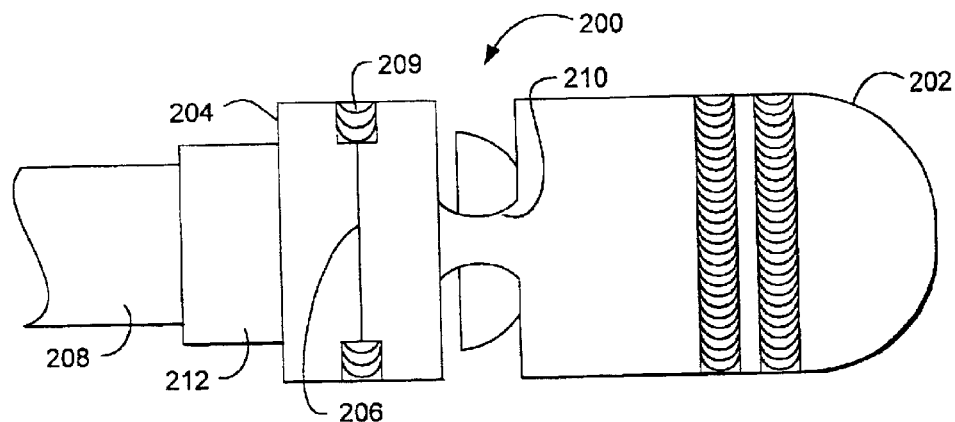
FIGS. 11A–C are side views of a deflecting member housing assembly with a hub and hinged deflecting members.
Figure 11B:
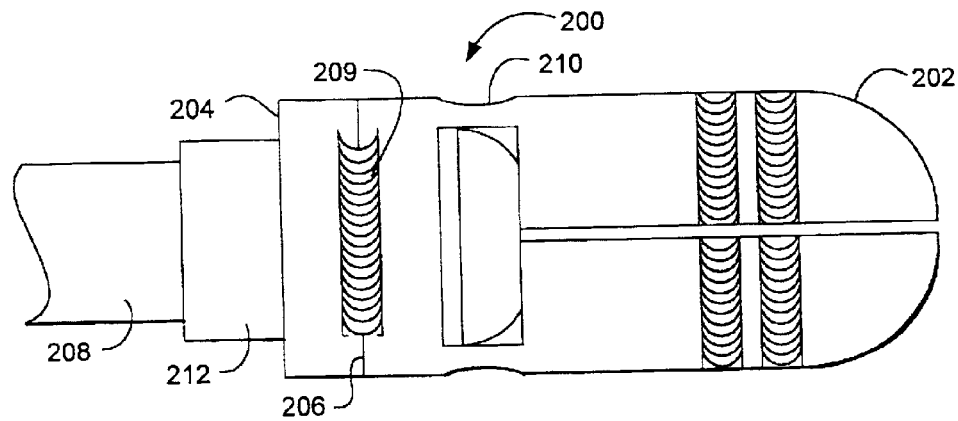
Figure 11C:
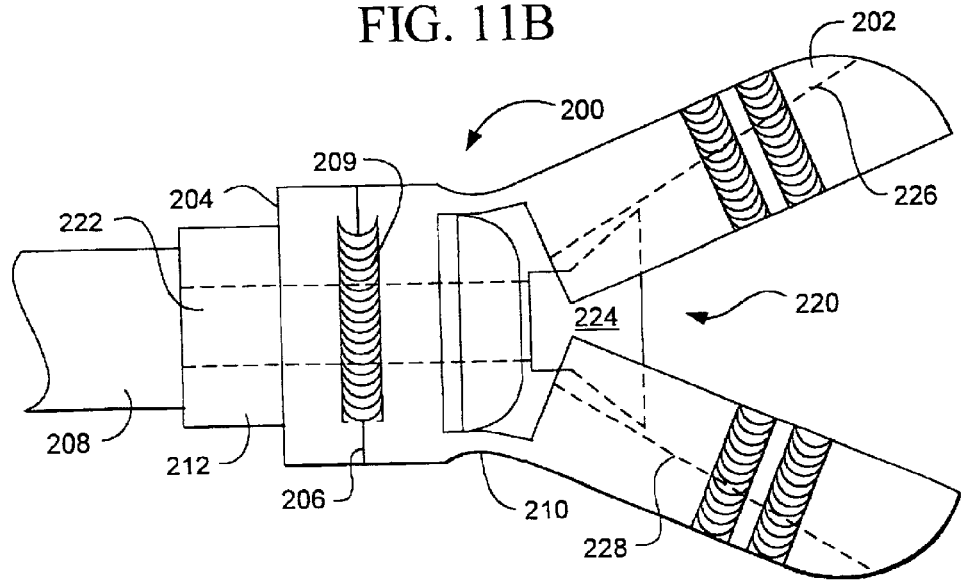

FIGS. 11A–C illustrate another embodiment of the invention that includes a vascular tissue expansion assembly 200 formed with hinged expansion members 202. The hinged expansion members 202 may be joined together around a circumferential portion or collar 204. The collar 204 may be also formed of multiple sections joined along a mating surface 206 by known methods such as welding or brazing techniques, and may be further attached or adhesively bonded to the relatively distal end of a catheter shaft 208. The collar sections may be joined together by spot welding at selected locations 209 around the circumference of the collar 204. Specific areas in proximity to the hinge section 210 of the expansion members 202 may be avoided to minimize significant thermal stress to this area, and to reduce interference with the free movement of the expansion members. The expansion members 202 may be similarly formed from several portions including a nosepiece or nosecone that are joined together by similar bonding or joining techniques. Although the illustrations provided include a pair of expansion members 202 joined to the collar, any number of members may be selected for the vascular tissue expansion assembly 200.

The typical finished diameter of the tissue expansion assembly 200 may range from approximately 0.030" to 0.090", including the range from 0.058" to 0.078", for coronary applications, and from approximately 0.080" to 0.100", including 0.091", for peripheral applications. Similarly, the finished length of the tissue expansion assembly 200 may range from approximately 0.150" to 0.250" for most coronary applications, and 0.200" to 0.600" for many peripheral applications. Other suitable dimensions for these components may be of course selected and modified for particular applications.

Each expansion member 202 shown in FIGS. 11A–B may include a hinge section 210 attached to a circumferential portion of the collar 204. The expansion members 202 and collar 204 may be formed separately or integrally. For example, the collar 204 and expansion members 202 may be formed of separate injection molded plastics or metals that are joined together. The collar 204 may be also cylindrically shaped, and may be connected with the expansion members 202 through other connective or hinged components that may be attached by soldering, welding or brazing or other joining techniques. Alternatively, the hinged expansion members 202 and collar 204 may be integrally formed from a single piece of selected material with techniques such as electronic discharge machining (EDM) or other formative methods well known in the art. The hinged expansion members 202 and collar 204 sections may be formed by removing selected portions of a unitary body of material selected for the expansion assembly 200. After the tissue expansion assembly 200 is formed, the entire assembly may be stress relieved by immersion in 520° C. potassium bath for two or more minutes followed by a room temperature water bath quench using known nickel titanium stress relief techniques. It should be understood that all components of the vascular tissue assembly 200, including the collar 204 and expansion sections 202, may be manufactured from biocompatible metals or engineered plastics such as Delrin, polycarbonate or ABS, or from formable metals such as stainless steel or nickel titanium alloys such as 45% cold-worked Guide BB nitinol supplied by Shape Memory Inc, CA.

As shown in FIGS. 11A–C, a catheter may be provided for treating a vascular occlusion consisting of an elongated shaft 208 formed with at least one lumen extending from the proximal section to the distal section of the shaft. One or more hinged spreading members 202 may be formed at the distal section of the shaft 208 as part of a vascular tissue displacing assembly 200. The distal section of the elongated shaft 208 may also include a hub 212. A collar section 204 may be fitted around the external surface of the hub 212. In addition, one or more hinged spreading members 202 may be joined to the collar section 204 as a unitary body. The distal most end of the spreading or tissue displacing member 202 may move away from the central or longitudinal axis of the shaft 208 to disrupt a vascular occlusion as illustrated in FIG. 11C. The spreading member 202 may be deflected by an actuating assembly 220 positioned along, or at least in a part of, the elongated shaft 208 to move the distal most end of the spreading member 202 in response to an actuation force. The tissue displacing member 202 may be configured to rotate about one end thereof away from the longitudinal axis of the catheter shaft 208 to displace tissue surrounding a vascular occlusion. The actuating assembly 220 may be configured to be operable from a relatively proximal section of the elongated shaft 208.

The actuating assembly 220 may include an actuation element 222 having a relatively distal end mounted cam 224 for communication with a cam follower formed in a spreading member 202 to urge the spreading member in a substantially lateral direction. The cam follower 226 may be formed along a relatively interior portion of the hinged spreading member 202. The cam 224 may be also formed with a cam edge 228 that slidably contacts the cam follower 226 formed on the interior portion of a spreading member 202 when the cam is moved in a relatively proximal direction. The distal most end of the spreading member 202 may be thus arcuately moved in a substantially lateral direction.

As shown in FIGS. 12A–B, an actuation member may move the deflecting members 242 of a tissue displacing assembly 230 between an open and closed position. An actuation member such as a pull tube 232 may move or actuate the deflecting or blunt end members 242 from a first closed position as illustrated in FIG. 12A, to a second open position, as illustrated in FIG. 12B. The deflecting members 242 may be distally joined to an intravascular catheter (not shown), and may be configured to remain in a closed position until the physician pulls back on the actuation member 232 in a relatively proximal direction. The intravascular catheter may be initially positioned in an artery using a guidewire such that the distal end of the deflecting member 242 is positioned adjacent to or at least partially within a vascular occlusion. Once positioned, the catheter may remain relatively fixed at a particular location within the artery by activating a stabilizing balloon (not shown) coupled to the catheter. The stabilizing member may apply a mechanical force to an arterial wall to provide a frictional force that acts on and tends to keep the catheter in place within the blood vessel. The stabilizing member may be an inflatable positioning or securing balloon that is in communication with, and inflated by, an inflation lumen formed in the catheter body, or an expandable anchoring assembly such as a shape memory metal basket. When the deflecting members 242 are eventually actuated and moved to an open position, the distal section of the deflecting member may spread apart or flare out in a substantially lateral direction away from the longitudinal axis of the catheter. A mechanical force is thus applied to the area surrounding a vascular occlusion or vessel wall by the deflecting members 242. A relatively large spreading force may be observed at the distal most end of the deflecting member 242 upon actuation. In various embodiments of the invention, the deflecting member assembly 230 may be configured to exert approximately as much as up to 60 to 330 pounds of force per square inch. The deflecting member assembly 230 may be further configured such that upon release of the pull member 232, the deflecting member 242 may return to a closed position either actively or passively.

The deflecting members 242 described herein may be activated by various actuation assemblies which spread apart or deflect the distal most region 244 of the members. An actuation assembly may be configured to produce lateral movement in each hinged spreading member 242 of a vascular tissue expansion assembly 230. Each spreading member 242 may include a cam follower 234 formed on its interior portion. For example, the deflecting members or jaws 242 may be actuated by a cam 236 and cam follower 234 assembly positioned within the relatively interior portion of the deflecting members. A cam follower 234 may be formed as an angled or curved surface on the interior surface of a deflecting member 242. A cam 236 may be attached to the distal end of an actuation member 232 that is positioned within a catheter shaft. The surface 238 of the cam may be formed with a variety of configurations including cylindrical, toroidal or spherical, and may have one or more shaped surface to communicate with a corresponding cam follower 234. The cam 236 may be also configured as a central hub internally positioned within the deflecting members 242. The cam 236 and cam follower 234 may be configured so that longitudinal movement of the actuation member 232, in either a proximal or a distal direction, causes the surface or edge 238 of the cam 236 to slidably move over the surface of the cam follower 234. A spreading or actuating force is thus imparted on the tissue expansion member 242 which opens or moves the distal end 244 of the deflecting member 242 in lateral direction with respect to the longitudinal axis of the catheter. The contours of the cam and cam follower surface may be configured to provide a selectable amount of lateral displacement or spreading force for the deflecting member 242. The ratio of lateral displacement of the deflecting members 242 per unit longitudinal movement of the actuation member 232 and cam 236 may vary greatly including a range from approximately 1:1 to 2:1.

Figure 13:
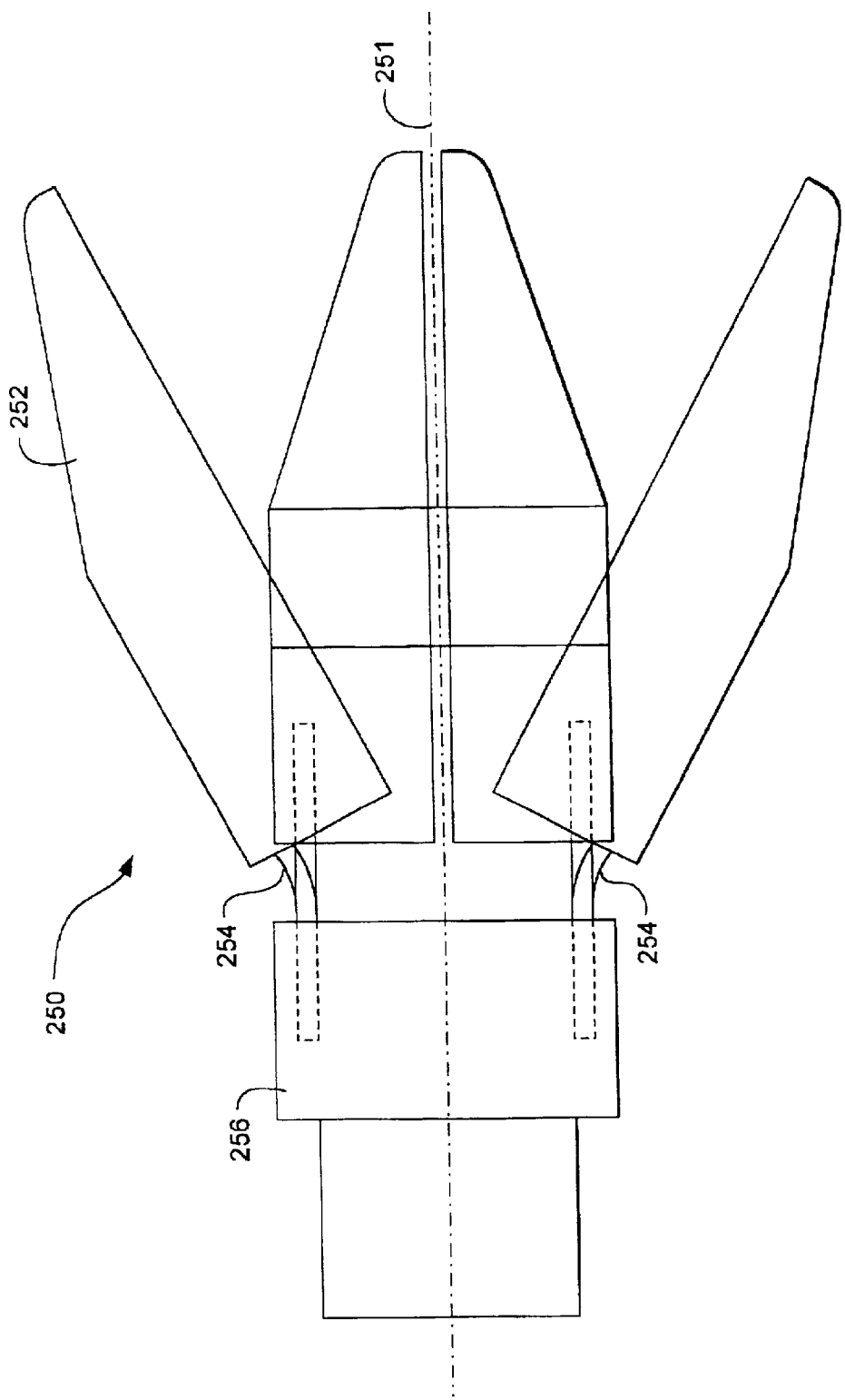
FIG. 13 is a simplified side view of a hinged deflecting member assembly shown in an open and closed position.

A hinged deflecting member assembly 250 may include a plurality of hinges 254 as shown in FIG. 13. Each individual deflecting member 252 may further include more than one hinge 254. The hinge section 254 of each expansion or deflection member 252 assist individual members in moving between relatively open and closed positions. The hinge 254 may also provide arcuate or eccentric movement of the expansion member 252 from a closed position to an open position with respect to the longitudinal or central axis 251 of a catheter. The hinge 254 may be biased so that the expansion member 252 may spread apart or deflect to an open position in response to an applied actuation force, which may range from but is not limited to approximately 0.25 to 8 lbs., and may return to a closed position once the applied force is removed. The spreading force may be applied to actuate the expansion members 252 by various mechanisms described herein such as pull or push tubes and wires, and cam assemblies (not shown). The deflection range of the expansion members 252 may vary according to selected applications, and may include a lateral bend or spreading angle of the tissue expansion member of up to 45° or greater with respect to the longitudinal axis 251 of the catheter.

The deflecting member assembly 250 shown in FIG. 13 may be integrally formed from a single piece of suitable material or may include a combination of different components. Each deflecting or spreading member 252 may be connected to a collar 256 with one or more hinges 254. Additional hinges 254 may provide additional lateral support for the deflecting member 252 when moving between open and closed positions. Each hinge 254 may be separately formed of nitinol wire or other flexible material, and may connect deflecting members to the collar 256. The collar 256 may be further mounted to a relatively distal portion of a catheter shaft (not shown).

Figure 14A:
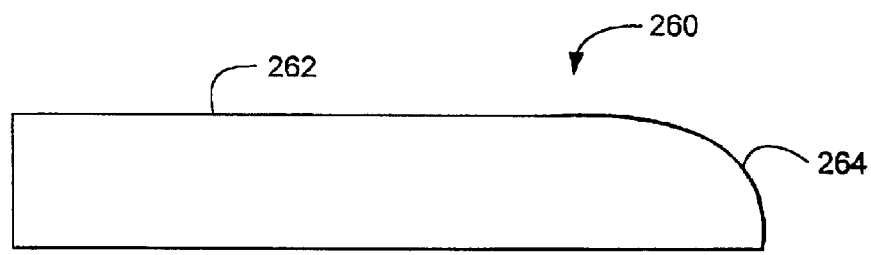
FIGS. 14A–D are simplified partial side views of various configurations for tissue expansion members.
Figure 14B:
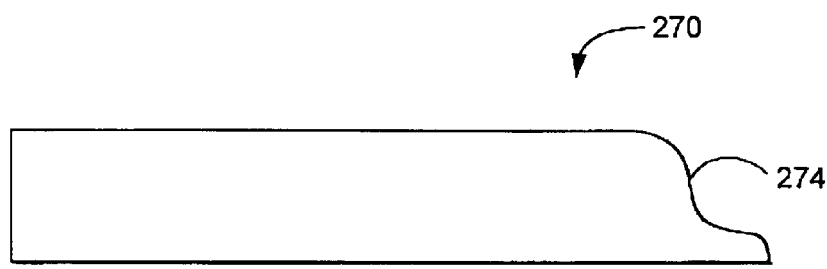
Figure 14C:
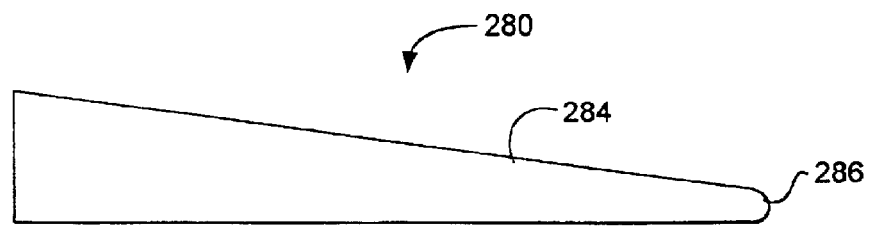
Figure 14D:
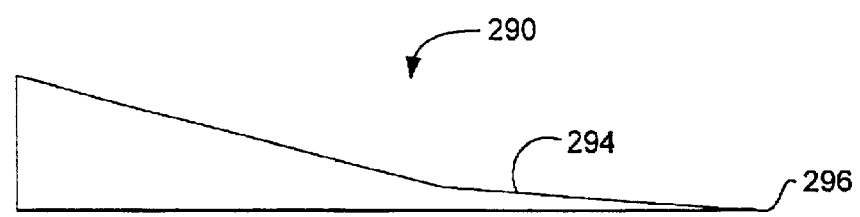

FIGS. 14A–D illustrate various configurations for tissue expansion members. As described above, vascular tissue expansion members may be formed with a wide variety of configurations and shapes. The expansion members 260 may be modified for particular applications, and may include various combinations of straight or linear proximal sections 262 with concave, and relatively atraumatic, curved distal portions 264 as shown in FIG. 14A. Alternatively, the distal portion 274 of the expansion member 270 may be formed with a convex curved distal end as illustrated in FIG. 14B. FIGS. 14C–D also provide other available modifications to the distal end sections 284 and 294 of expansion members 280 and 290 having a linearly and non-linearly tapered profiles, respectively, which may terminate with variably pointed tips 286 and 296 at the distal most ends of the expansion members. Other configurations may be of course selected for the vascular tissue expansion members described herein for particular applications.

The expandable displacement assemblies described herein may be actuated by various mechanisms. As illustrated in FIGS. 15A–B, for example, distal mounted spreading members 302 may be actuated with an actuating balloon 304 that spreads open the distal end portions 306 of spreading members. The spreading or deflecting members 302 may be deflected in a relatively outward direction by the inflatable actuation balloon 304 disposed within the deflecting member housing 300. The actuation balloon 304 may be coupled to a relatively distal portion of a catheter 308, and may be inflated through an inflation lumen in communication with an inflation device coupled to the proximal end of the catheter (not shown). The actuation balloon 304 may be made of known materials including high strength polymers such as PET or irradiated polyethylene, and may be configured for multiple inflations to desired pressures. The actuation balloon 304 may be configured to exert enough force on the interior surface of deflecting members 302 to produce a spreading force of up to approximately 60 to 330 pounds of force per square inch or more. As with other pulling or pushing actuation assemblies described herein, the spreading force may be modified according to applied pressure and the relative size of deflecting members 302 and the internally positioned actuation balloon 304 which may have an inflated profile of approximately 0.050" to 0.200".

An intravascular tissue expanding catheter, as shown in FIGS. 15A–B, may include a catheter shaft 308 having at least one lumen or conduit extending along the longitudinal axis of the catheter shaft. A housing 300 may be formed at the distal end of the catheter shaft 308 wherein the housing may include at least one hinged deflecting member 302 having a distal most tip 306 that moves in a substantially lateral direction away from the central axis of the shaft to expand an area surrounding a vascular occlusion. The deflecting member housing 300 may be further constructed from multiple pieces or may be formed from a unitary piece of deformable material. A slit 310 formed in the housing 300 may basically provide a pair of deflecting members 302 with integrally formed hinges. The selected material should support the opening and closing movements of deflecting members 302, and should be relatively rigid enough to apply the desired deflective force. An actuation assembly such as an expandable balloon 304 may be positioned along at least some portion of the catheter shaft 308, or within the housing 300, to move or deflect the hinged deflecting member 302 away from the central axis of the shaft. An inflation conduit may be of course formed along the longitudinal axis of the catheter shaft 308 leading to the expandable balloon 304.

Figure 16A:
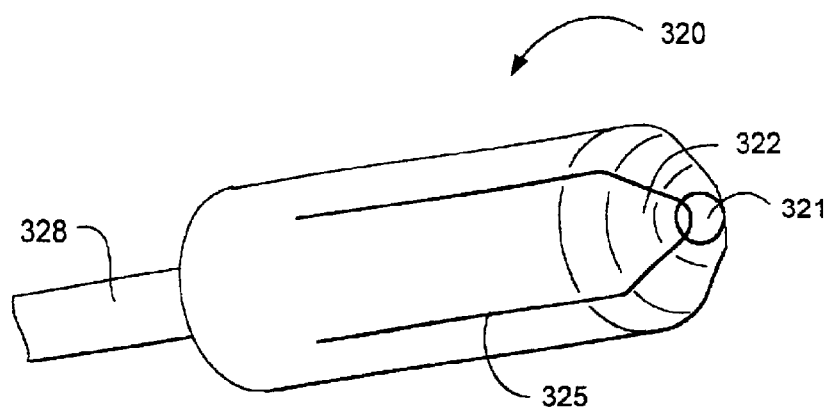
Figure 16B:
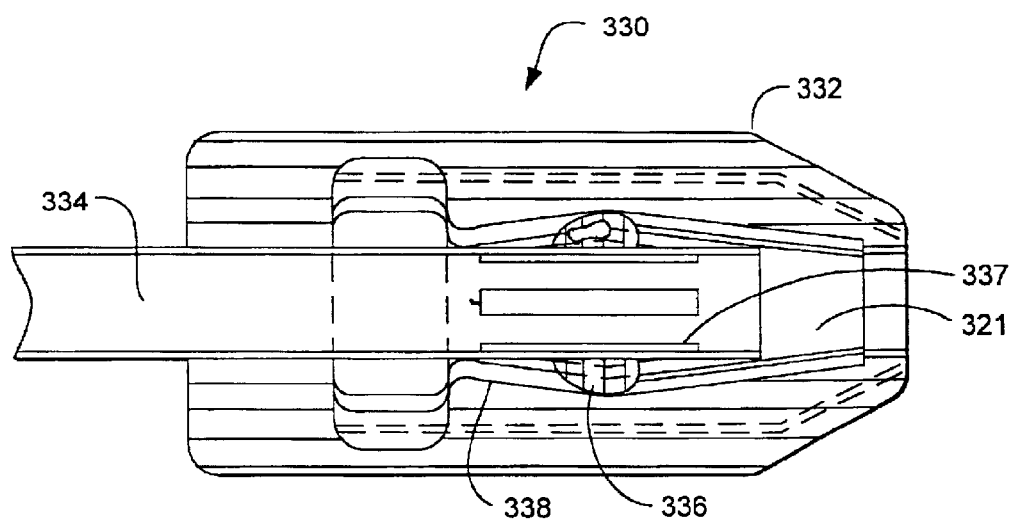

FIGS. 16A–D illustrate various tissue displacement assemblies formed with a plurality of deflecting members. The displacement housing assembly 320 shown in FIG. 16A may be formed from single piece of formed material, and may include multiple slits or openings 325 created by techniques described herein to form several deflecting members 322 that spread open when activated. The deflecting member assembly 320 may be mounted along a relatively distal portion of a catheter shaft 328. An actuation member 334 positioned within the assembly housing 330, as shown in FIG. 16B, may include a cam 336 formed with a central hub or curved surface for communication with cam followers 338 formed along the interior portions of deflecting members 332. The actuation member 334 may include a threaded section 337 that directs the cam 336 in a relatively distal or proximal direction when rotated in a particular direction. The housing 330 may further include threaded portions matching the threaded section 337. The cam 336 may be moved in a relatively proximal direction by rotating the threaded tube 334 to open or urge the deflecting members 332 apart so that the cam 336 slidably contacts adjacent cam followers 338 to spread apart the hinged spreading members 332. The deflecting members 332 may be similarly closed by rotating the threaded tube 334 in a relatively opposite direction.

FIGS. 16C–D illustrates another deflecting member assembly 340 formed with deflecting members 342 that have multiple hinges 343. The assembly 340 housing may be also formed from a unitary piece of material, and may include formed openings that accommodate arcuate movement of the deflecting members 342. A cam 346 may be internally positioned within the housing 340, and may slidably contact cam followers 348 formed along the inner surface of deflecting members 342. The cam 346 may be connected to a pull tube 344 at a relatively distal section, and may be directed in a relatively proximal direction to spread apart the hinged deflecting members 342. The deflecting member housing 340 may provide a pinless or rivetless hinged section that supports deflection of at least one deflecting member 342 when the pulling element 344 is pulled in a proximal direction. The actuation tubes and assemblies shown in FIGS. 16A–D may be also formed with a guidewire lumen 321 to permit the passage of a guidewire when the deflecting member assembly is either opened or closed. As with other cam configurations described herein, the internally positioned cams may be formed of a variety of configurations including spherical, frusto-conical or semi-planar.

Figure 17A:
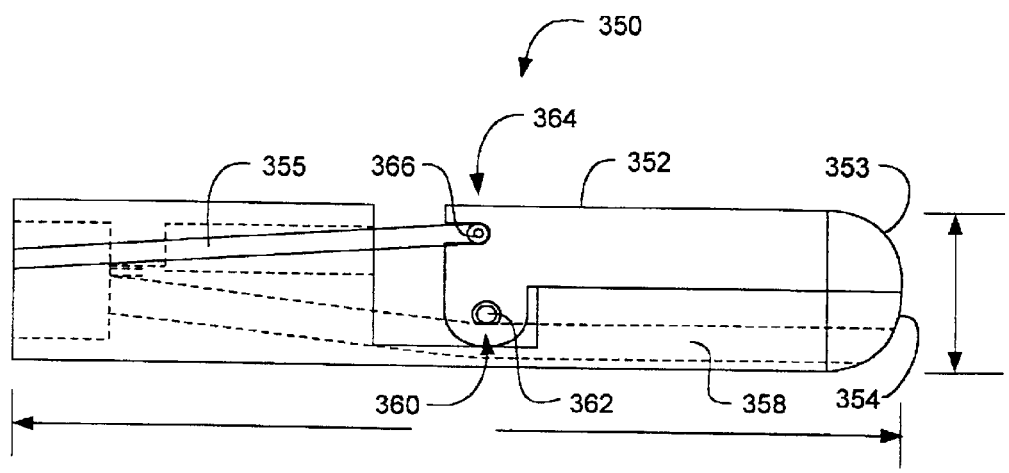
FIGS. 17A–B are side views of a vascular tissue expansion assembly with a single hinged member connected to a pulling element.
Figure 17B:
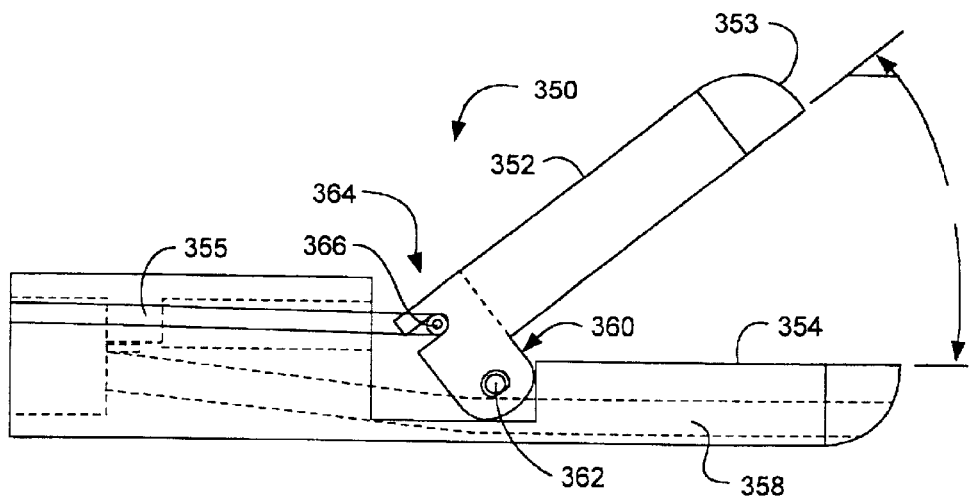

The tissue expansion catheters described herein may also include single hinged tissue displacing members 352 that are connected to an actuation or pulling element 355 as illustrated in FIGS. 17A–B. The tissue expansion assembly 350 may comprise a hinged upper expansion member 352 and a relatively fixed lower extension 354 of the assembly 350. The tissue expansion member 352 may include a hinge pin assembly 360, and may be pivotally attached to the lower extension 354 with a hinge pin 362. The hinge pin assembly 360 may comprise a hinge pin socket formed along a section of the upper expansion member 352 that may be aligned with a corresponding hinge pin socket formed along the lower extension 354. A hinge pin 362 may fit through both sockets to allow the upper expansion member 352 to rotate about the hinge pin. The hinge pin 362 may be externally threaded over a portion of its length, and may be securely fastened into either socket, or held in place by press fit, by a nut or other mechanical attachment known in the art. The longitudinal position of the hinge pin 362 may be positioned along any portion of the expansion member assembly 350, and may be located about 0.200" to 0.400" from the distal end of the assembly. The lower extension 354 of the tissue expansion assembly 350 may be formed with a proximal tubular section and an elongated distal most section that includes a socket to receive the hinge pin 362 for rotatably connecting the upper expansion member 352. The lower extension 354 may also contain a lumen 358 along at least a portion of its length for the placement and advancement of a guidewire.

As shown in FIG. 17B, the upper expansion member 352 may be spread apart or opened so that the distal end 353 of the expansion member is moved laterally with respect to the longitudinal axis of the catheter. The tissue expansion member 352 may be actuated by an attached pull wire 355. The pull wire 355 may be rotatably attached to a relatively proximal portion of the upper expansion member 352 by a pull wire pin and socket assembly 364. The pull wire 355 may be of course attached to other portions of the upper expansion member 352, and may be fastened with other known fastening method including welding or brazing techniques. Additionally, the pull wire or member 355 may be formed of stainless steel or other suitable materials, and may be formed with a flattened distal end section having a pull wire pin hole. The flattened distal end section may fit into a corresponding slot or groove formed with corresponding pull wire pin holes in the upper expansion member 352. A pull wire pin 366 may be press fit or otherwise secured in place to hold the pull wire 355 and the upper expansion member 352 together. The upper expansion member 352 may pivot about the hinge pin 362 in response to a directed pulling force to the attached pull wire 355 applied in a relatively proximal direction. The spreading angle of the tissue expansion member 352 may vary according to particular applications and may range up to 45° or more. The hinge pin 362 and the pull wire pin 366 may be fabricated from hardened stainless steel or other suitable metals. It will be appreciated that other hinge configurations and known pivoting mechanisms may be equally applicable to this and other related embodiments described herein.

Additional intravascular catheters formed in accordance with the principles of the invention are illustrated in FIGS. 18A–D. The catheters may each include a catheter body formed with at least one conduit and a single tissue expanding member connected to the distal section of the catheter body. The expanding or deflecting member 368 may be defined by a relatively proximal portion and a relatively distal portion. Upon actuation, the distal portion of the expanding member 368 may be configured to rotate about or spread apart relative to its proximal portion. The distal section of the catheter may further include a relatively fixed extension 362. The relatively proximal portion of the tissue expanding member 368 may be connected to the fixed extension 362 with a hinge pin 366 to permit the relatively distal portion of the tissue spreading member to rotatably move away from the fixed extension. As shown in FIGS. 18A–B, a guidewire lumen 363 may be formed in a lower extension member 362 that is concentric or centered with respect to the longitudinal axis of the catheter 360. As shown in FIG. 18B, the guidewire lumen 363 may thus fit in between the pull wire pin 364 and the hinge pin 366 which are both positioned substantially across the expansion member assembly. This configuration may provide a relatively large guidewire lumen 363 to accommodate a wide variety of guidewires or devices with diameters of up to 0.035" or greater. The guidewire lumen 363 may further include an inner liner tube or guidewire tube extension 365 that may extend along the full length or discrete sections of the catheter 360 or the lower tissue expansion member 362. The inner liner tube 365 may be formed from a variety of materials including nitinol, high strength polymers such as polyimide, lubricious polymers such as Teflon. The hinged deflecting member 368 may be also formed with a curved or contoured surface to fit around the inner liner tube 365 when it is placed in closed position as shown in FIG. 18B. Alternatively, as shown in FIGS. 18C–D, the guidewire lumen 363 may be positioned off-center with respect to the axis of the catheter 370. In this configuration, the hinge pin 366 may be positioned in between the pull wire pin 364 placed across the upper expansion member 368 and the guidewire lumen 363 when viewed in cross-section as shown in FIG. 18D. Similarly, an inner lining tube 365 may be positioned within the guidewire lumen 363, and may extend along the entire length or discrete portions of the catheter shaft and/or expansion member assembly.

Figure 19A:
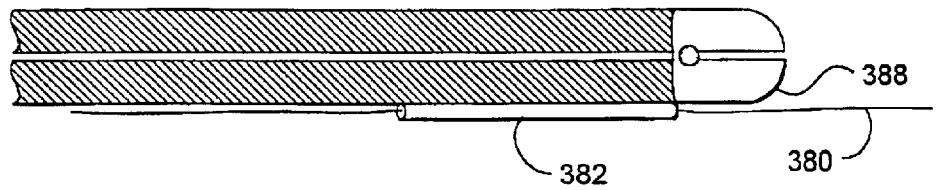
FIGS. 19A–E are simplified side and cross-sectional views of a catheter shaft with distally mounted expansion members and guidewire guiding pathways.
Figure 19B:
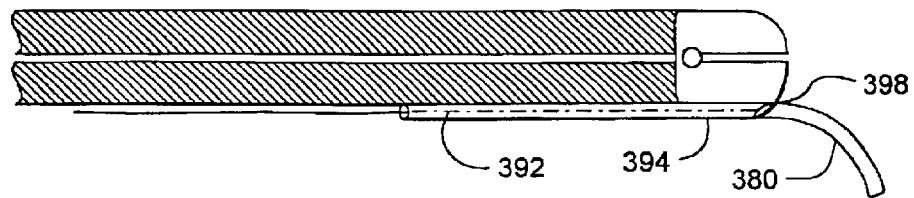
Figure 19C:
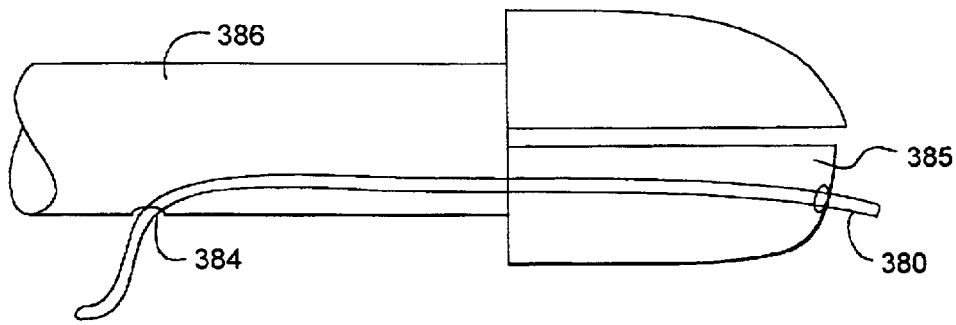
Figure 19D:
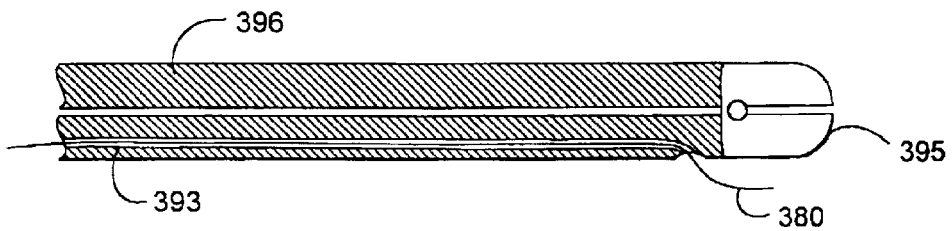
Figure 19E:
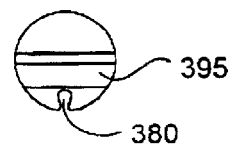

A guidewire 380 may be passed through various lumens formed along different portions of the intravascular catheters described herein as shown in FIGS. 19A–E. Although a guidewire may be commonly used to position the catheters in an area near a vascular occlusion, a guidewire may be of course positioned through a portion or across the obstruction after the occlusion is displaced by device. The intravascular catheter may further include a guiding tube externally attached to a section of the catheter or along the entire length of the catheter. As shown in FIG. 19A, a guiding tube 382 may be positioned along a relatively distal portion of the catheter to receive a guidewire 380. The guiding tube 382 may terminate prior to the proximal section of a lower expansion member 388 so that the guidewire 380 exits the guiding tube proximal to the lower expansion member. Alternatively, as illustrated in FIG. 19B, the guiding tube 392 may extend into, or may be coupled to, another guidewire lumen 394 formed in a relatively lower extension member 398 such that a guidewire 380 exits from the distal end of lower extension member. The guidewire guiding tube 392 can be made from a wide variety of materials including formable polymers such as polyimide and polyethylene, or from a metal hypotube made of stainless steel or nitinol. As shown in FIG. 19C, a guidewire lumen 384 may also extend along at least a distal portion of the catheter shaft 386 and an expansion member 385. FIGS. 19D–E illustrates a guidewire lumen 393 formed in the catheter shaft 396 and partially within an expansion member 395. The guidewire lumen 393 in the expansion member 395 may be enclosed or partially exposed to the exterior surface of the catheter. At least a distal portion of the catheter may thus ride along a guidewire 380 in a monorail fashion. These and similar configurations for positioning a guidewire lumen are included herein including other different regions along the catheter shaft and expansion member assembly.

Figure 20A:
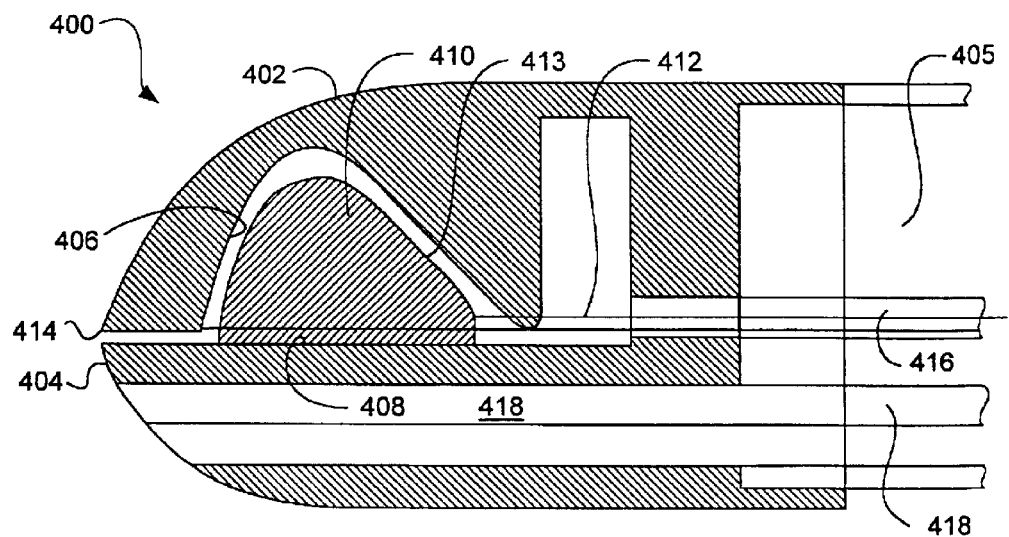
FIGS. 20A–C are simplified cross-sectional side views of a vascular tissue expansion assembly with various actuation and cam assemblies for deflection of a single hinged deflecting member.
Figure 20B:
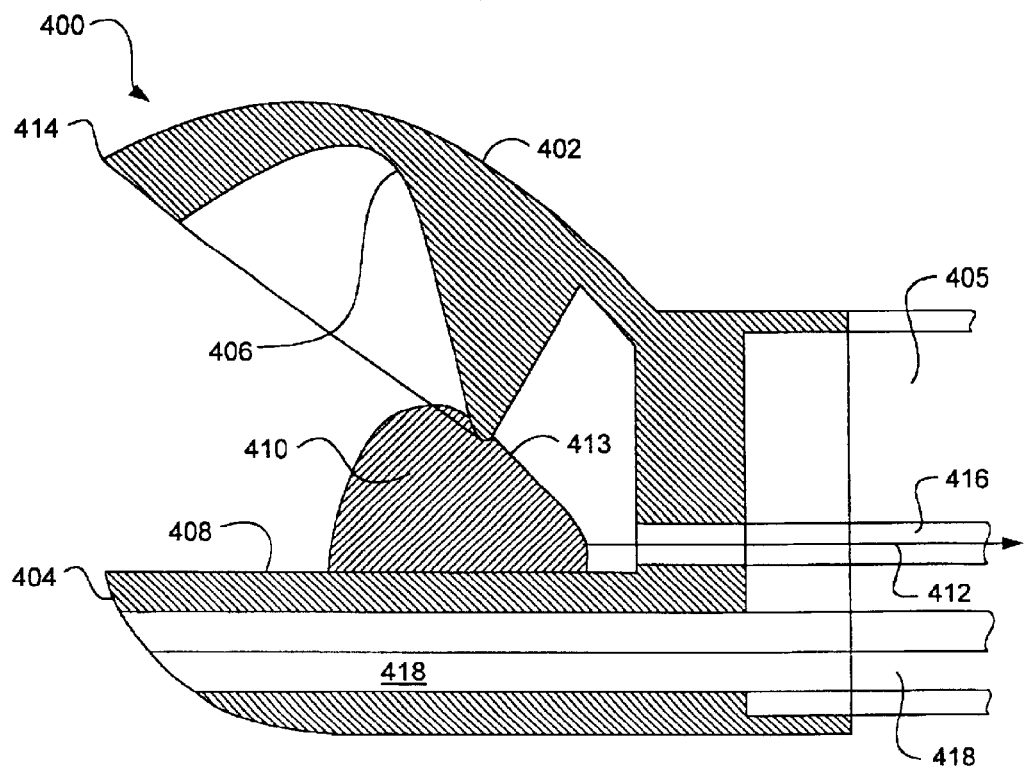
Figure 20C:
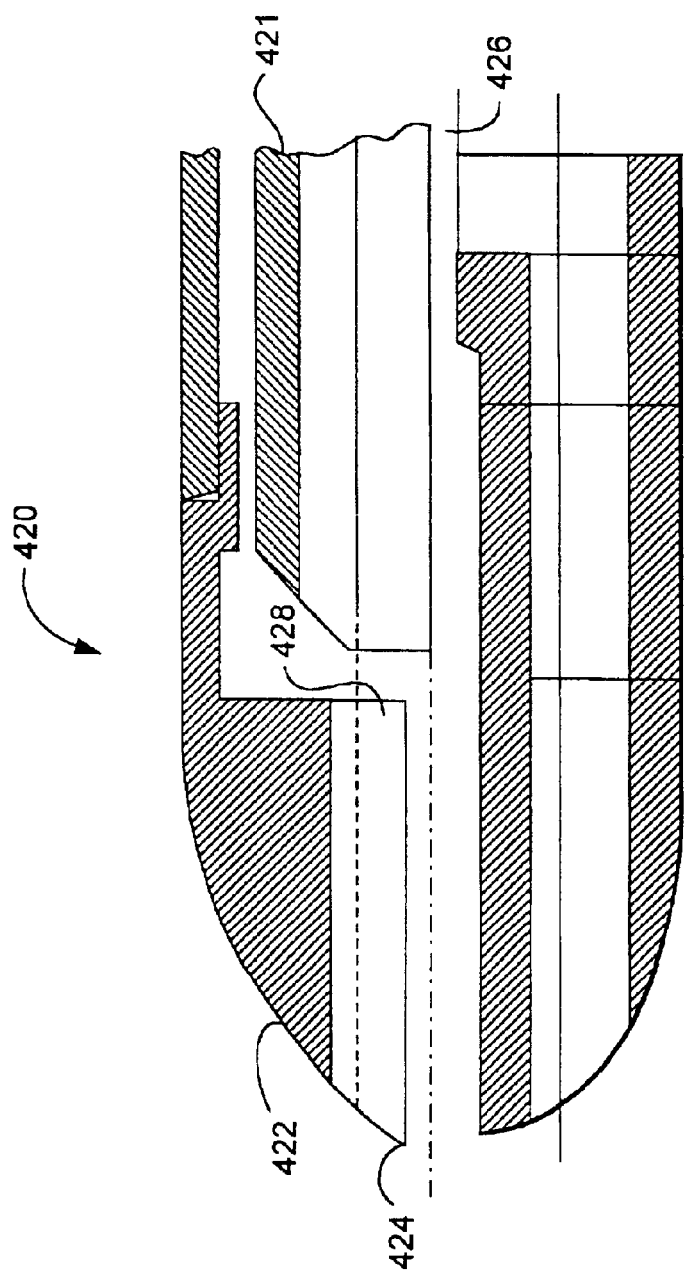

FIGS. 20A–C illustrate other vascular tissue expansion assemblies formed in accordance with the invention. The tissue expansion assembly 400 shown in FIGS. 20A–B may include a single hinged spreading member 402 formed by methods similar to those previously described. The hinged spreading member 402 may include a curved interior portion formed with a cam follower 406. The distal section of the catheter shaft 405 or the expansion assembly 400 may also include a relatively fixed or stationary extension 404 formed with a cam follower having a co-linear bearing surface 408 with respect to the longitudinal axis of the catheter. A cam 410 formed with complementary surfaces 413 may be internally positioned with the tissue expansion assembly 400. The cam 410 may be configured for slidable movement along the co-linear bearing surface 408 and the internal cam follower 406 formed along an interior portion of the single hinged spreading or deflecting member 402. An actuation member or pull wire 412 may be connected to the cam 410 to move the distal most tip 414 of the spreading member 402 in a substantially lateral direction away from the longitudinal axis of the catheter. An actuation conduit 416 may be formed along a portion of the expansion assembly 400 and the catheter shaft 405. The pulling element or pull wire 412 may be positioned relatively proximal to the cam 410 within the actuation conduit 416. A guidewire lumen 418 may be similarly formed through at least a portion of the expansion assembly 400 or catheter shaft 405.

The cam assembly shown in FIGS. 20A–B may include an irregularly shaped cam 410 and cam follower 406 formed on a single hinged deflecting member 402. A wide variety of configurations may be selected for the cam 410, which may be symmetrical and asymmetrical as shown herein, and may include one or more contoured or relatively linear surfaces 413. The cam follower 406 may be formed by machining the interior surface of the deflecting member using various known techniques including precision machining methods such as CNC or EDM techniques. The cam follower 406 and deflecting member 402 may be alternatively manufactured and formed from a cast heat treated metal part or molded plastic part. The cam 410 may be formed of stainless steel or engineered plastics such as polycarbonate, Delrin or Teflon with high strength and relatively low surface friction. The cam 410 may be also attached to an actuation member 412 such as a pull tube using adhesive bonding, crimping, soldering, welding or other joining well known methods. The surfaces of the cam and/or cam follower may be also coated with a lubricous polymer coating such as Teflon to reduce friction therebetween.

FIG. 20C illustrates another tissue displacement assembly 420 that may be positioned along a relatively distal portion of an intravascular catheter. A push tube 421 may be positioned within the actuation conduit 426 to deflect the distal end 424 of the displacing member 422 away from the catheter axis in response to a distally directed force. The push tube 421 may be positioned relatively proximal to a cam follower 428 within the actuation conduit 426 which may be formed of a variety of linear or curved surfaces. As described earlier, these various actuation mechanisms described herein may be used in accordance with other aspects and variations of the invention.

Figure 21A:
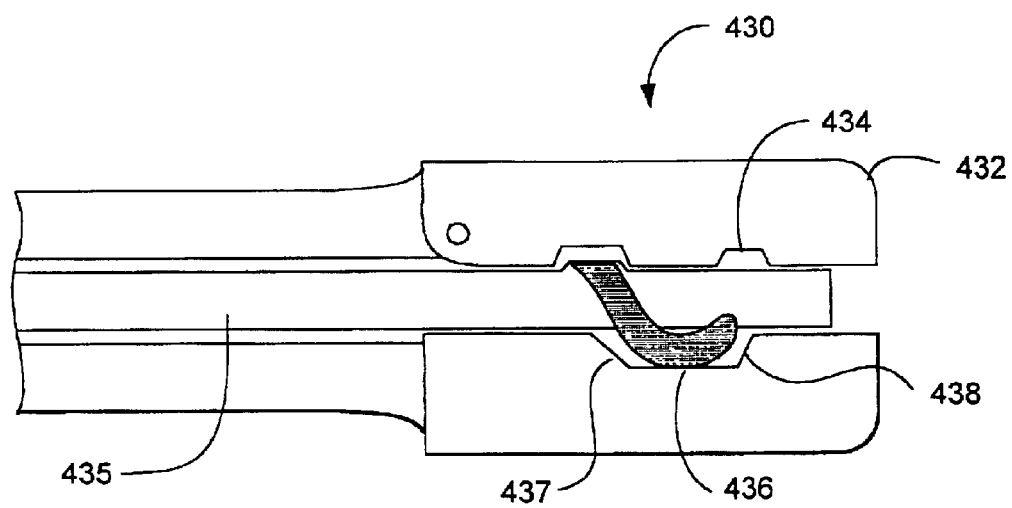
FIGS. 21A–B are side and cross-sectional views of a hinged expansion member that may be rotationally actuated.
Figure 21B:
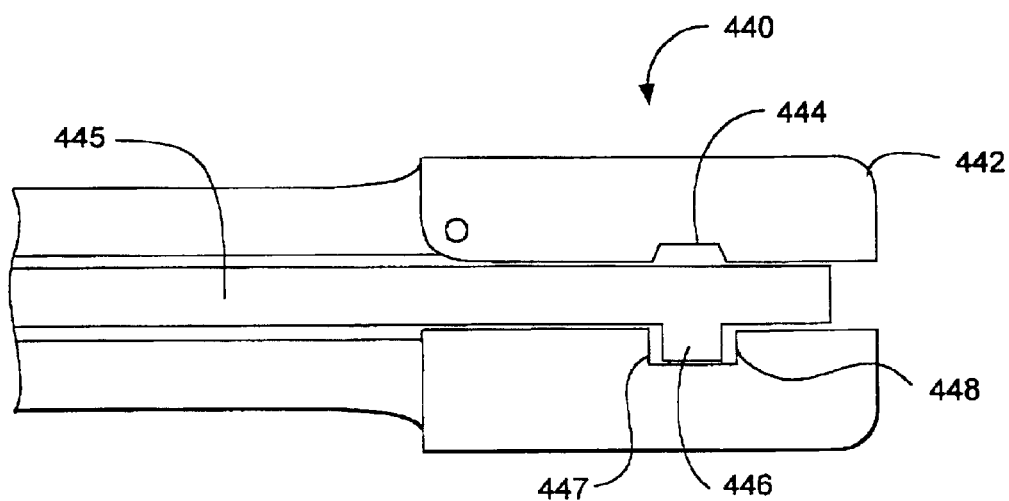

A rotationally actuated deflecting assembly 430 and 440 is further provided in accordance with the invention as shown in FIGS. 21A–B. The lateral movement of the vascular tissue expansion member may be generated by a rotational movement of an actuation member about the longitudinal axis of the catheter. As shown in FIG. 21A, the cam follower 434 may be formed as a spiral groove on the interior surface of at least one expansion member 432. The cam 436 may include a spiral thread or ridge attached to the actuation member 435. The vascular tissue assembly 430 may further include a relatively fixed extension 438 formed with another cam follower having complementary grooves 437. When the actuation member 435 is rotated about the catheter axis, the cam 436 may contact the cam followers 434 and 437 and spread apart the expansion member 432. Alternatively, as illustrated in FIG. 21B, the cam follower 444 may be formed as a groove or notch along the interior portion of the tissue expansion member 442. The relatively fixed extension 448 of the expansion assembly 440 may be also formed with a cam follower 447 with a enlarged groove. A cam 446 may include an offset curved surface or protuberance that slidably fits within the groove of the extension 448 when the expansion member 442 is in a closed position. However, when the actuation member 445 is rotated about the catheter axis, the curved cam 446 surface may slidably rotate and communicate with the cam followers 444 and 447 to spread open the expansion member 442. Although the illustrations provided show single expansion members, it is understood that similar rotational actuation mechanisms may be applied to assemblies with multiple expansion members.

FIGS. 22–24 provide various catheter shaft configurations that may be selected for the intravascular devices described herein. An intravascular catheter for expanding tissue may basically include a body that is formed with an outer reinforced shaft coaxially formed about an inner coiled body for column load reinforcement of the catheter body. The inner coiled body may be also formed with an actuation conduit. The catheter may further include a distally mounted tissue expanding member and an actuation element positioned within a conduit formed within the catheter shaft. The catheter shaft may exhibit a unique combination of dimensional and mechanical properties that permit their passage through tortuous vasculature including coronary, cerebral or peripheral blood vessels. The flexibility and column load bearing characteristics of these catheter shafts support the transmission or delivery of sufficient spreading or disrupting forces to push through or spread apart obstructed vascular regions in order to form channels across an occlusion. The dimensional properties of the intravascular catheters include a relatively small diameter throughout the length of the devices, and a relatively low-profile to minimize obstruction of circulatory function. The structural and mechanical properties of the catheter shafts further include a combination of compressive and torsional strength with sufficient rigidity, together with lateral flexibility, particularly at the more distal sections of the catheter. The outside diameter for the relatively distal end portions of the catheter may widely range for particular applications including from approximately 0.014" to 0.200". For coronary applications, the outer diameter may range from approximately 0.014" to 0.092", including a preferable range of 0.039" to 0.78". For peripheral applications, a range of 0.070" to 0.200" may be selected. The materials and construction of the catheter may be configured to allow the medical practitioner to transmit the required or appropriate longitudinal force from a remote or proximal end of the relatively small diameter catheter across a substantial distance to a relatively distal end portion of the catheter. An actuation member such as a pull wire or tube may be directed in a relatively proximal direction at a remote or proximal location to spread apart or deflect distal mounted tissue displacing members. This may be accomplished, in part at least, through the use of a relatively stiff shaft to support the column load which may be formed from high density polyethylene or polyimide, and wire braid or stiffening wire. The catheter may also have a sufficient length to position the hinged deflecting members in the coronary or peripheral vasculature from a femoral, brachial or carotid approach. Typical lengths for these applications include, but are not limited to, a range from about 60 to 200 cm, including a preferable range for coronary applications from 120 to 160 cm. A preferable working length of 80 to 120 cm may be selected for peripheral applications. The vascular tissue expanding assembly may be positioned in various blood vessels such as coronary, cerebral and peripheral arteries. Expanding members may be maneuvered to and positioned at or near the anastomoses or juncture of a bypass graft and a coronary artery, including at or near a substantially occluded artery. The intravascular catheters provided herein may re-establish a channel or lumen of sufficient size in the native blood vessel to provide a pathway for placement of a guidewire across a total occlusion for subsequent use with primary therapies such as PTA, PTCA, and stenting.

The catheter shaft may basically include an outer catheter shaft formed with a longitudinal shaft lumen. An inner coiled body may be positioned within the longitudinal shaft lumen for column load reinforcement of the outer shaft. The inner coiled body may be also formed with a longitudinal coiled lumen to receive a pulling element or tube to actuate a distally mounted tissue displacement assembly. The movable pulling element may be slidably positioned within the longitudinal coiled lumen for relative movement of the pulling element with respect to the inner coiled body. This inner coiled and outer shaft configuration may provide flexibility and improved transmission of columnar force over the length of the catheter. The relatively distal portions of the catheter may be thus advanced into narrowed and tortuous vasculature including coronary blood vessels where distal mounted vascular tissue expansion assemblies may be actuated to provide a spreading force to displace a vascular occlusion.

The outer catheter shaft may be formed of various durable material or suitable polymers and have a reinforcing member positioned around the exterior walls of a catheter. The outer catheter shaft may be braid reinforced, and may have an outer diameter ranging from approximately 0.025" to 0.080". Of course, these dimensions may vary according to particular applications. The reinforcing member may be a braided shaft member to improve the overall torsional strength of the catheter shaft. The reinforcing member may be a metal braid, a hypotube or a stiffened polymer tube such as HDPE. The reinforcement member may be also formed of a flat stainless steel wire braid coated with polyurethane which is, in turn, disposed over an inner core of polyimide (available from HV Technology, GA). Alternatively, the reinforcement member may be formed of a stainless steel braid encapsulated in pebax tubing available from TFX Medical Corp., NH.

The inner diameter of the lumen formed in the outer shaft may be varied, and may range between approximately 0.028" to 0.030" or more to accommodate a coiled inner shaft. A coiled inner shaft may have an appropriate outer diameter to fit within the outer shaft, and may range between approximately 0.027" to 0.029" or more. These relative dimensions may be of course varied for particular vascular applications. In a preferable embodiment, the force transmission characteristics of the coiled shaft may be achieved with an outer diameter that is no more than 0.003" smaller than the inner diameter of the outer shaft. The coiled shaft may be further constructed of stainless steel or steel with a silicon content as high as 2%, and may be formed with a tight pitch wind that may provide intimate contact between adjacent coils. The coiled shaft may transmit or sustain a columnar force of up to 50 lbs without significant coil filer overlap or increase in the outer diameter of the coiled shaft. The inner coiled body may be closely wound, and may have a proximal portion that includes a hypotube.

The pull member may be a pull tube made of stainless steel or a hypotube formed of nitinol available from Memry Inc., CA. The pull member may be selected or configured to limit the amount of longitudinal force applied by the physician to the vascular tissue expanding assembly. A preselected amount of force may be established for the pull member so that amounts of force applied in excess of the selected limit will merely deform the pull member and will not be transmitted to expanding members. A preferable range for a predetermined amount of longitudinally applied force may include between 5 to 10 lbs of force. This may be achieved by configuring a pull tube to elastically deform at loads at or near 5 to 10 lbs with complete elastic recovery for strains up to 8%. This property can be achieved by the use of super elastic metals such as nitinol provided by Shape Memory Alloys, Inc., CA.

Figure 22A:
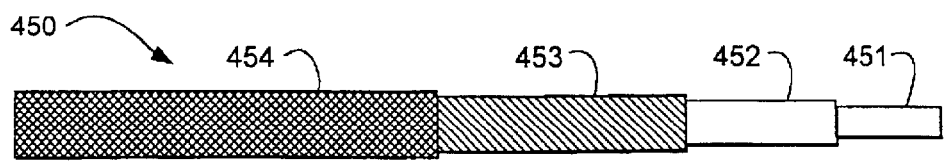
FIGS. 22A–24A are simplified side views of a various catheter shaft configurations.
Figure 22B:
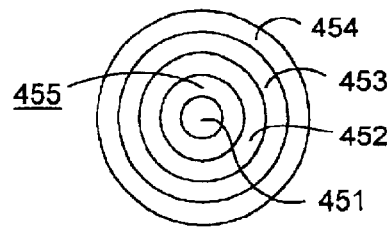

The positioning of the actuation or pull member, the guidewire, and the coil, may be varied with respect to the central axis of the catheter. These components may be located concentrically or off-center within the catheter body. In one embodiment, as shown in FIGS. 22A–B, the catheter shaft 450 may be formed with a concentric or coaxial design with respect to both the pull member 452 and the guidewire 451 relative to the catheter central axis. The outer catheter shaft 454 may be formed with a single lumen to accommodate an inner coiled shaft 453. The inner coiled shaft 453 may be similarly formed with an coiled shaft lumen for slidable movement of a pull member or pull tube 452. The pull tube 452 may be also formed with a lumen 455 for positioning of a guidewire 451 therethrough. The inner diameter of the outer shaft 454 may accommodate the inner coiled shaft 453. Similarly, the inner diameter of the inner coiled shaft 453 may provide for slidable movement of a pull tube 452. The pull tube 452 may also have a sufficient inner diameter to allow slidable movement of a guidewire 451 positioned therein. The inner coiled shaft 453 may allow the overall catheter shaft 450 to sustain the transmission of a columnar or longitudinal force over the length of the catheter without a substantial compression of the catheter shaft and resultant loss of force transmission. The outer shaft body 454 may assist in retaining the coiled shaft 453 in proper alignment to avoid coil filer overlap. The filers within the coiled shaft 453 may not be necessarily rounded, and may be relatively flat to provide an increased contact surface with neighboring coils. The inner coiled shaft 453 may thus provide increased flexibility over a similarly dimensioned tube while providing sufficient column load bearing properties to the catheter shaft 450 without significant increase in the diameter of the coiled shaft due to the overlapping of adjacent coils when the force is applied. This overall construction may allow the catheter shaft to transmit torque and sustain a column load while still providing sufficient flexibility to a physician to navigate a catheter device through tortuous vasculature.

Figure 23A:
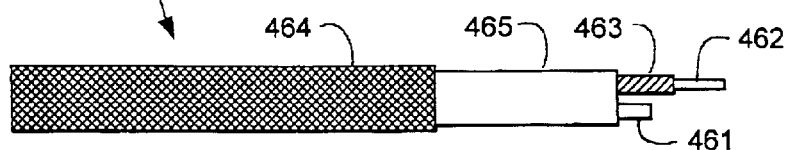
Figure 23B:
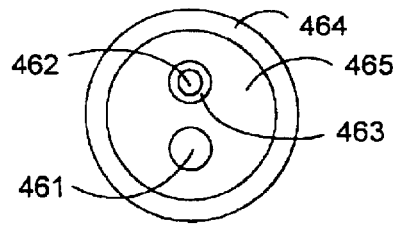

As shown in FIGS. 23A–B, a catheter shaft 460 may include one or more lumens longitudinally extending over the entire length or along a predefined portion of the catheter. The lumens may be adapted for the placement and advancement of various devices including guidewires, pull wires, spring wires, catheters, and optics. The catheter may further include ports for the delivery of gas and fluids such as air, saline, and contrast solutions. In various embodiments of the invention, catheter shafts may include lumens that are concentrically or eccentrically (off-centered) formed within the catheter. A wide range of available geometries for the lumens are of course available and may include but is not limited to cross-sectional shapes that are circular, semi-circular or oval shaped.

An inner shaft 465 may be extruded from polyethylene or similar material with a dual lumen configuration to provide a guidewire lumen and a separate pull tube or wire lumen. A coil 463 may include a pull tube or wire lumen and contain an actuation member 462 disposed therein. A guidewire 461 and pull tube or wire 462 may thus have an eccentric or off-center relationship. The guidewire lumen and pull tube lumen may be of course formed in other positions relative to one another within the inner shaft. The inner catheter body 465 may be formed from a variety of flexible medical polymers including polyimide, pebax, polyethylene, polyurethane, silicone. Additionally, pliable metal hypotubing such as stainless steel or nitinol may be selected which may be both polymer coated. The inner shaft 465 may be formed from copolymers and other combinations of the aforementioned polymers known to those skilled in the art, and may be formed by known extrusion methods with single or multiple lumens. The catheter body may also comprise multi-laminated tubing or joined longitudinal sections of tubing made from one or more of the aforementioned polymers and components.

The catheter shaft 460 illustrated in FIGS. 23A–B may include a reinforced outer catheter shaft 464 formed with an outer shaft lumen, and an inner shaft 465 positioned within the outer shaft lumen that is formed with an actuation lumen and at least one inner shaft lumen. A column load reinforcement coil 463 formed with a coil lumen may be positioned within the actuation lumen, and an actuation wire 462 may be slidably positioned within the coil lumen to provide relative movement of the wire. The coil 463 may further include an additional sleeve (not shown) surrounding the coil or coil lumen. An inner shaft lumen may be configured for placement of a guidewire 461, and may be formed in a side-by-side or non-concentric configuration relative to the actuation lumen.

Figure 24A:
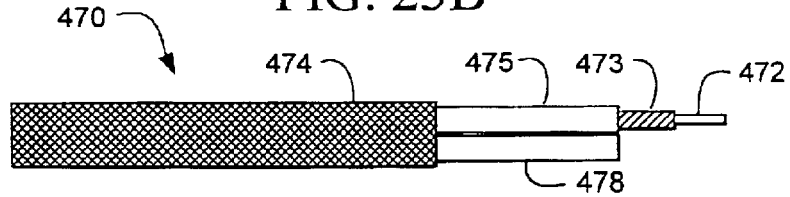
Figure 24B:
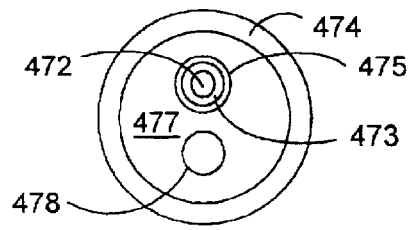

FIGS. 24A–B illustrate an outer catheter shaft 470 that may include two separate internal conduits or tubes 475 and 478 for a guidewire, and for a pull tube and coil assembly. The reinforced catheter body 470 may include a braid reinforced catheter shaft 474 formed with a longitudinal catheter shaft lumen 477. An actuation conduit 475 may be formed with a longitudinal actuation conduit lumen, and may be positioned along with a guidewire conduit 478 within the longitudinal lumen 477 of the catheter shaft. Moreover, a coiled support tube 473 formed with a coiled tube lumen may be positioned within the actuation conduit lumen for column load reinforcement of the actuation conduit 475. A pulling element 472 may also be positioned within the coiled tube lumen for relative slidable movement within the support tube 473.

Figure 25A:
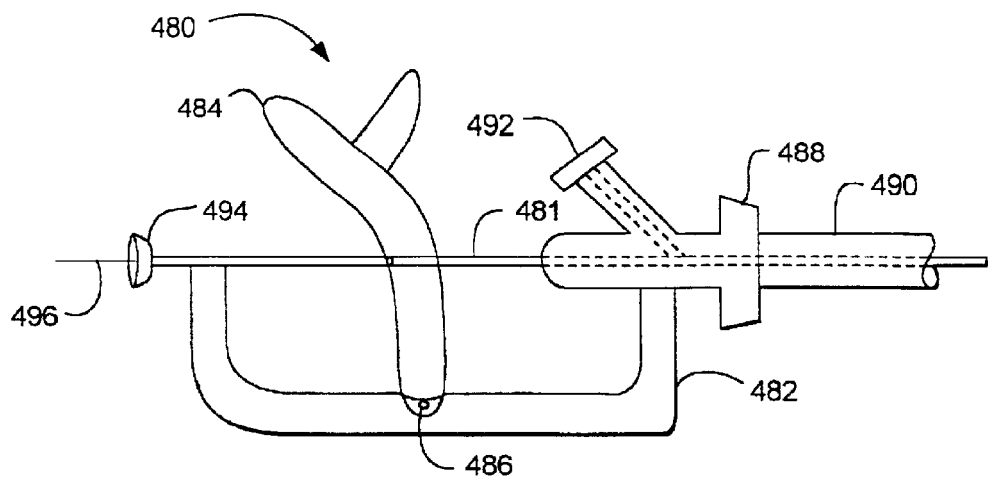
FIGS. 25A–C are simplified perspective views of a proximally positioned actuation assembly formed with a lever for use by an operator.
Figure 25B:
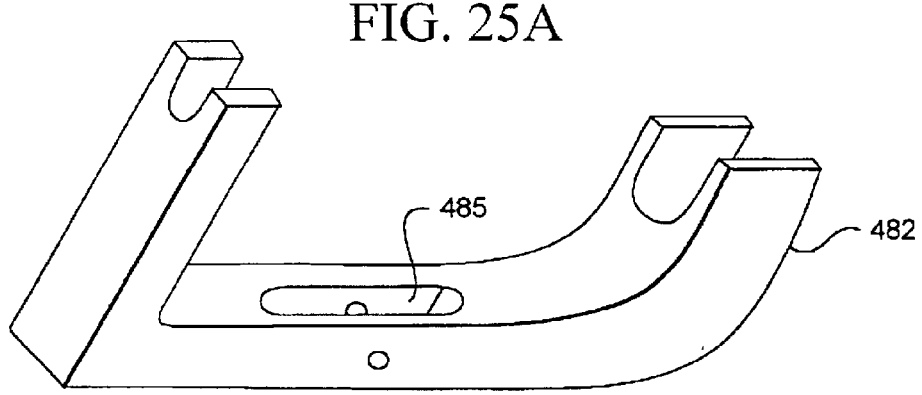
Figure 25C:
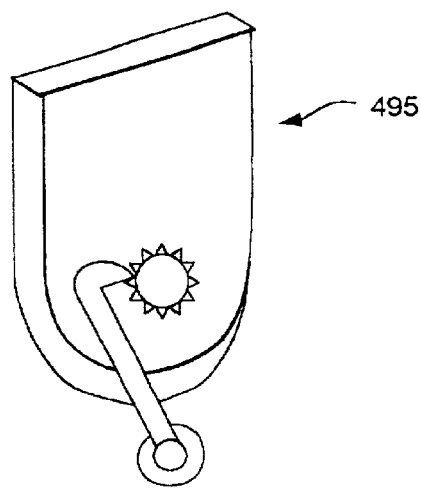

As shown in FIGS. 25A–C, the actuation or pull members 481 described herein may be coupled at its proximal end to a pulling mechanism 480 to provide longitudinal movement of the member. The pulling mechanism 480 may comprise a handle 482 that is pivotally attached to a lever arm 484 with a lever pin 486. The lever arm 484 may be fixedly attached to a proximal adaptor 488 that is further connected to the proximal end of a catheter 490. The lever 484 may fit into the handle 482 at a slot 485 as illustrated in FIG. 25B. The dimensions of the slot 485 may be selected with respect to the relative dimensions of the mating end of the lever 484 to limit the longitudinal movement of the lever to a predetermined or fixed amount. In a related embodiment shown in FIG. 25C, a ratchet mechanism 495 may be employed at the mating surfaces of the handle 482 and the lever 484 to control the longitudinal movement of the lever 484 to fixed increments.

The proximal adaptor shown in FIG. 25A may include one or more ports 492 for passage of a variety of materials described herein including fluid and gas introduction. The ports 492 may further have O-ring valves or luer fittings at their relatively proximal ends to provide improved seals. One or more ports 492 may have lumens which are fluidically or spatially coupled to lumens within the catheter 490. The proximal adaptor 488 may be made of an injection molded plastic or other commonly used materials. The proximal end of the pull member 481 may be attached to the lever 484 so that when the lever is pulled proximally by a physician, the lever pulls the pull member proximally. The handle 482 and lever 484 may be made from high strength injection molded plastics or other suitable materials. For embodiments utilizing a pull tube 481, the proximal end of the pull tube may be attached to the proximal end of the handle 482. The pull tube 481 may further include a guidewire introducer 494 attached at its proximal end to facilitate introduction of a guidewire 496 into the pull tube. The introducer 494 may have various configurations including a cone or funnel shape, and may be made from lubricious plastics.

Figures 26A, 26B:
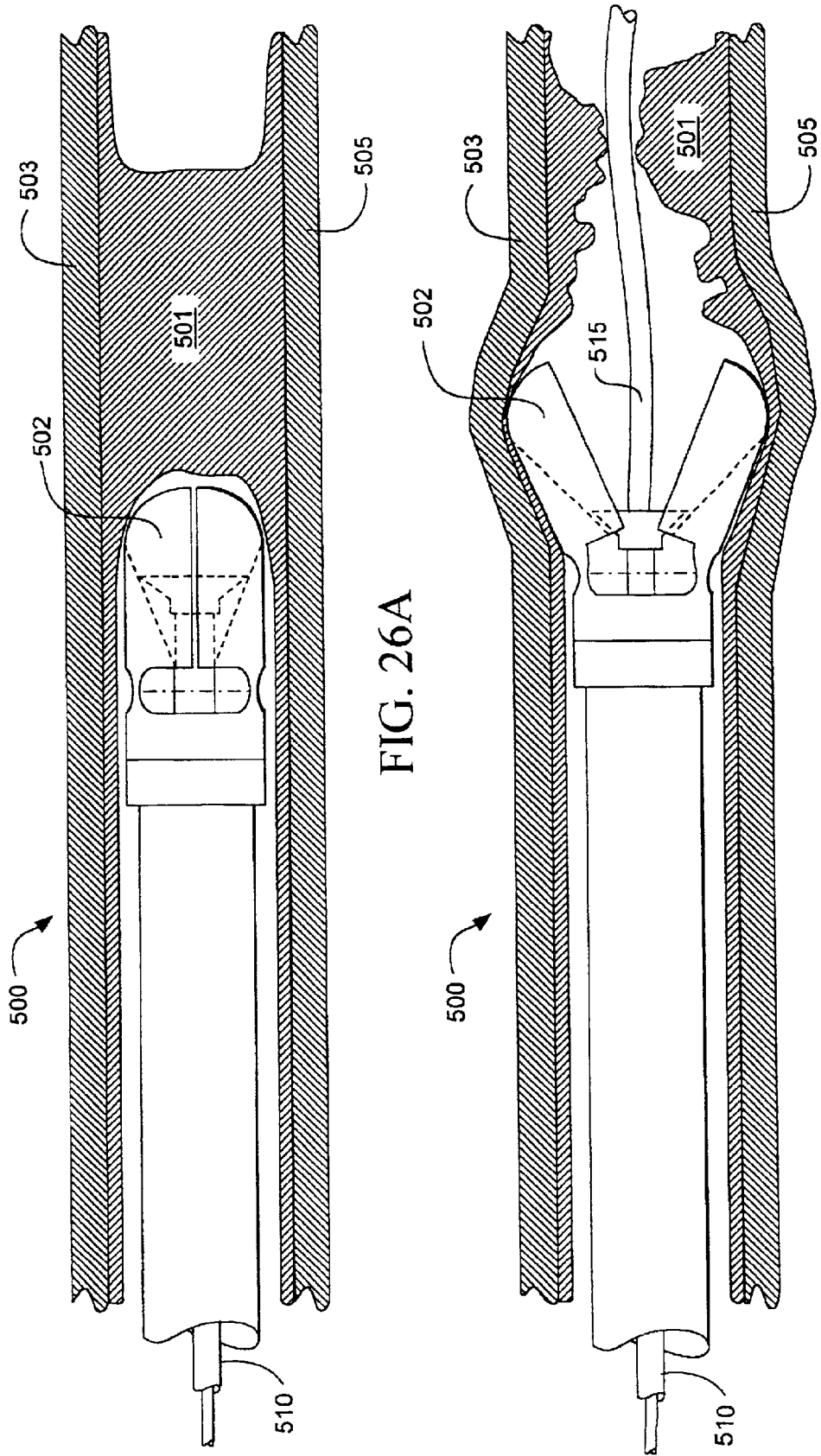
FIGS. 26A–B are cross-sectional views of an expansion member assembly having multiple deflecting members within an occluded blood vessel in an open and closed position.

Another aspect of the invention provides methods of displacing or disrupting a vascular occlusion as shown in FIGS. 26A–B. An intravascular catheter 500 may be selected having one or more spreading members 502 positioned at the distal region of the catheter that is responsive to directed force along the longitudinal axis of the catheter. The directed force may be provided by an actuator assembly 510 positioned along the catheter to transmit or relay a directed force applied from a relatively proximal portion of the catheter to the relatively distal spreading member 502. The vascular catheter 500 illustrated in FIG. 26A may be positioned adjacent to a substantially or totally vascular occlusion 501 in an initially closed position within a selected blood vessel 503. As shown in FIG. 26B, a directed force may be applied through the actuator assembly 510 to deploy or spread apart the spreading members 502 into an open position in order to displace the vascular occlusion 510. The spreading member 502 may displace or disrupt tissue surrounding or in the vascular occlusion 501 to create a path substantially through or around the occlusion. The blood vessel wall 505 may be also stretched to create a path substantially between the occlusion 501 and the blood vessel wall. When a vascular occlusion is adhered to the wall of the selected blood vessel, the spreading member 502 may possibly spread apart the separate the layers of the blood vessel wall 505. Some or all of these conditions may occur when displacing a vascular occlusion in accordance with apparatus and methods provided herein which often results in providing a path formed with the least or minimal amount of mechanical resistance. In addition, the vascular catheter 500 may be distally advanced along the path formed through or around at least a portion of the occlusion 501. A guidewire 515 may be alternatively selected and passed through a lumen or conduit to the site of the occlusion 501, and may be advanced around or through at least a portion of the occlusion. The vascular catheter 500 may be removed from the blood vessel 503 before or thereafter, or may be even maintained in position to carry out desired procedures such as placement of the guidewire 515 across the occlusion 501 through the dissected channels provided by the catheter. This separation or displacement of an occlusion within a blood vessel may be attributed at least in part to the difference in elasticity of a vascular occlusion and a blood vessel wall. For example, deposited plaque within arterial walls may be considered relatively brittle compared to relatively stretchable arterial wall. The obstruction may be thus fractured or broken up with reduced risk of compromising the blood vessel wall.

Figure 27A:
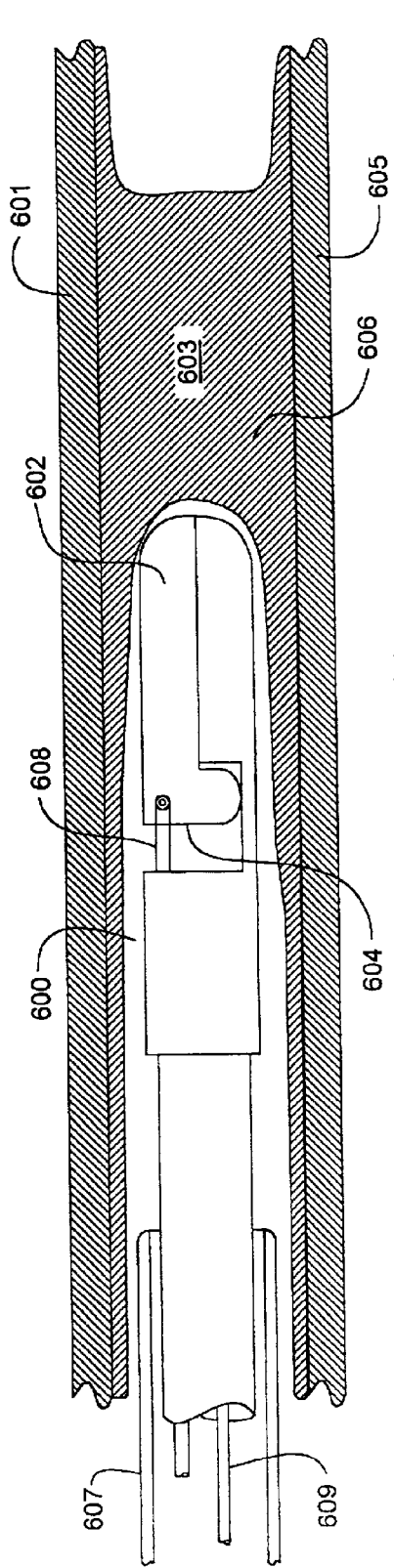
FIGS. 27A–B are cross-sectional views of an expansion member assembly having a single deflecting member within an occluded blood vessel in an open and closed position.
Figure 27B:
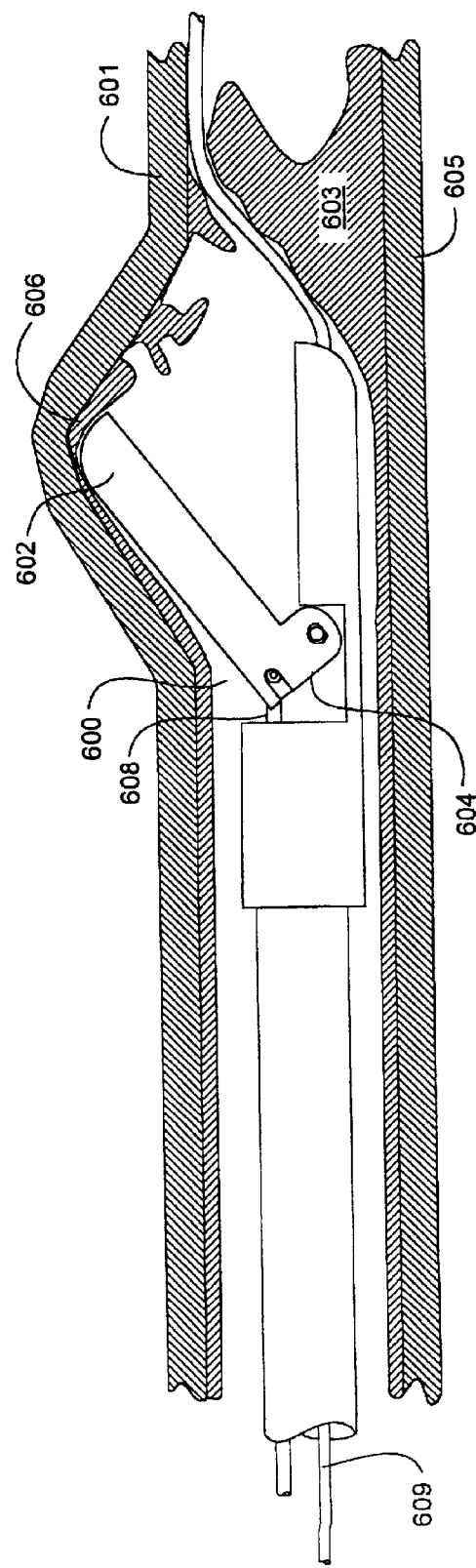

Another method of crossing a substantially occluded blood vessel is further provided in accordance with the invention as illustrated in FIGS. 27A–B. An intravascular catheter may be selected having a distally mounted tissue displacing assembly 600. The assembly 600 may include at least one tissue displacing member 602 having a relatively proximal portion 604 and a relatively distal portion 606 so that the distal portion is configured to expand relative to the proximal portion of the expanding member. The tissue displacing member 602 may be also configured to rotate about one end thereof. An actuation assembly 608 may be positioned within the intravascular catheter to transmit a spreading force to expand the distal portion 606 of the expanding member 602. The tissue expanding member 602 may be placed within a target blood vessel 601 in proximity to an occlusion 603. A guiding catheter 607 may be selected to position the intravascular catheter as shown with or without a guidewire 609. The tissue displacing assembly 600 may be activated so that displacing member 602 may extend and stretch the area surrounding blood vessel wall 605 thereby disrupting the occlusion 603 to permit the passage therethrough. The distal portion 606 of the tissue expanding member 602 may have an original diameter before actuation, and the distal portion 606 may expand to an enlarged diameter that is equal to at least approximately one-hundred and ten percent of its original diameter. The tissue displacing member 602 may be also controllably activated to provide intermittent expansion, and may be eventually deactivated thereafter and removed from the blood vessel 601.

Figure 28A:
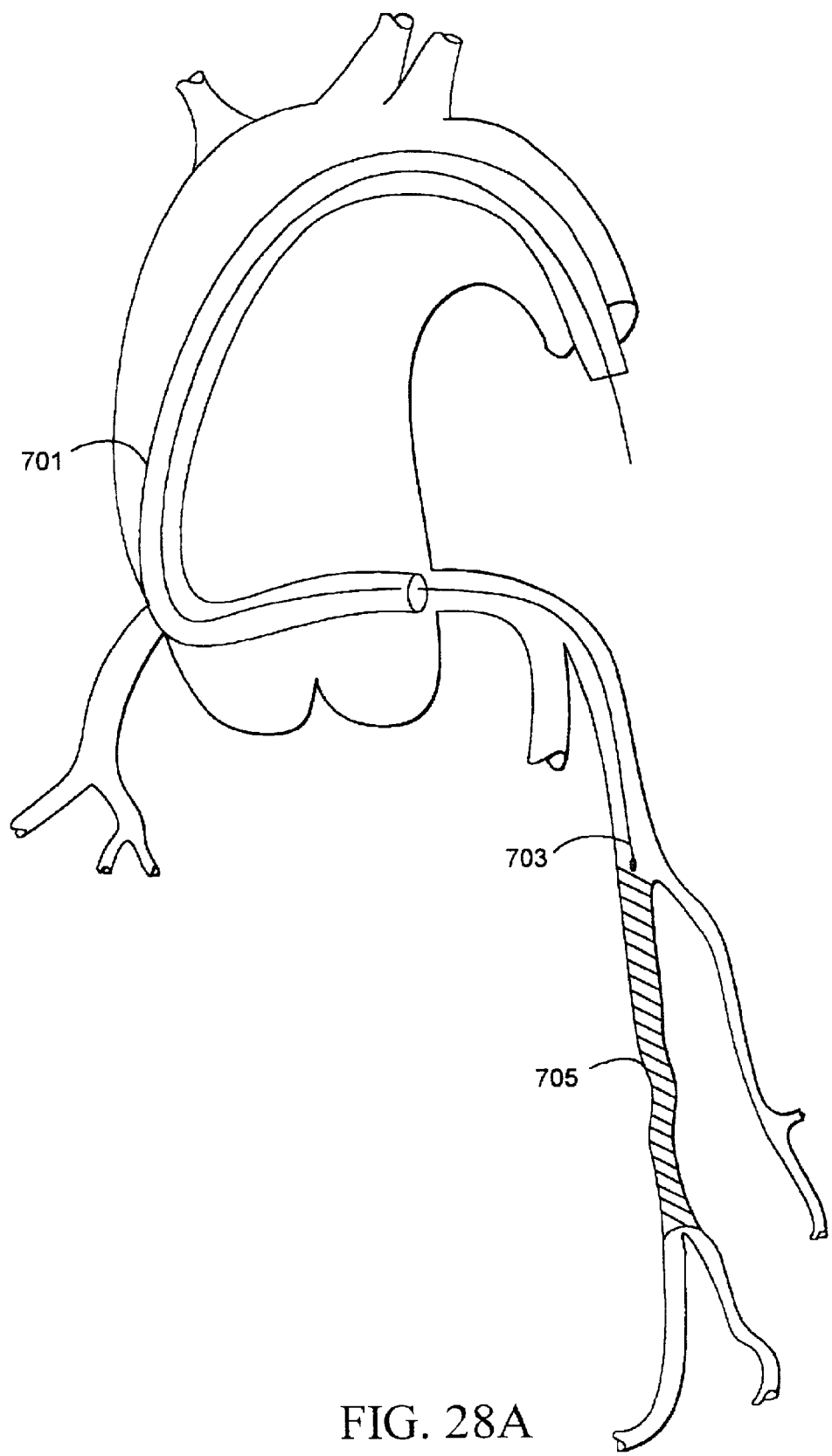
FIGS. 28A–I are simplified diagrams illustrating methods for crossing a coronary occlusion with apparatus and procedures provided in accordance with the invention.
Figure 28B:
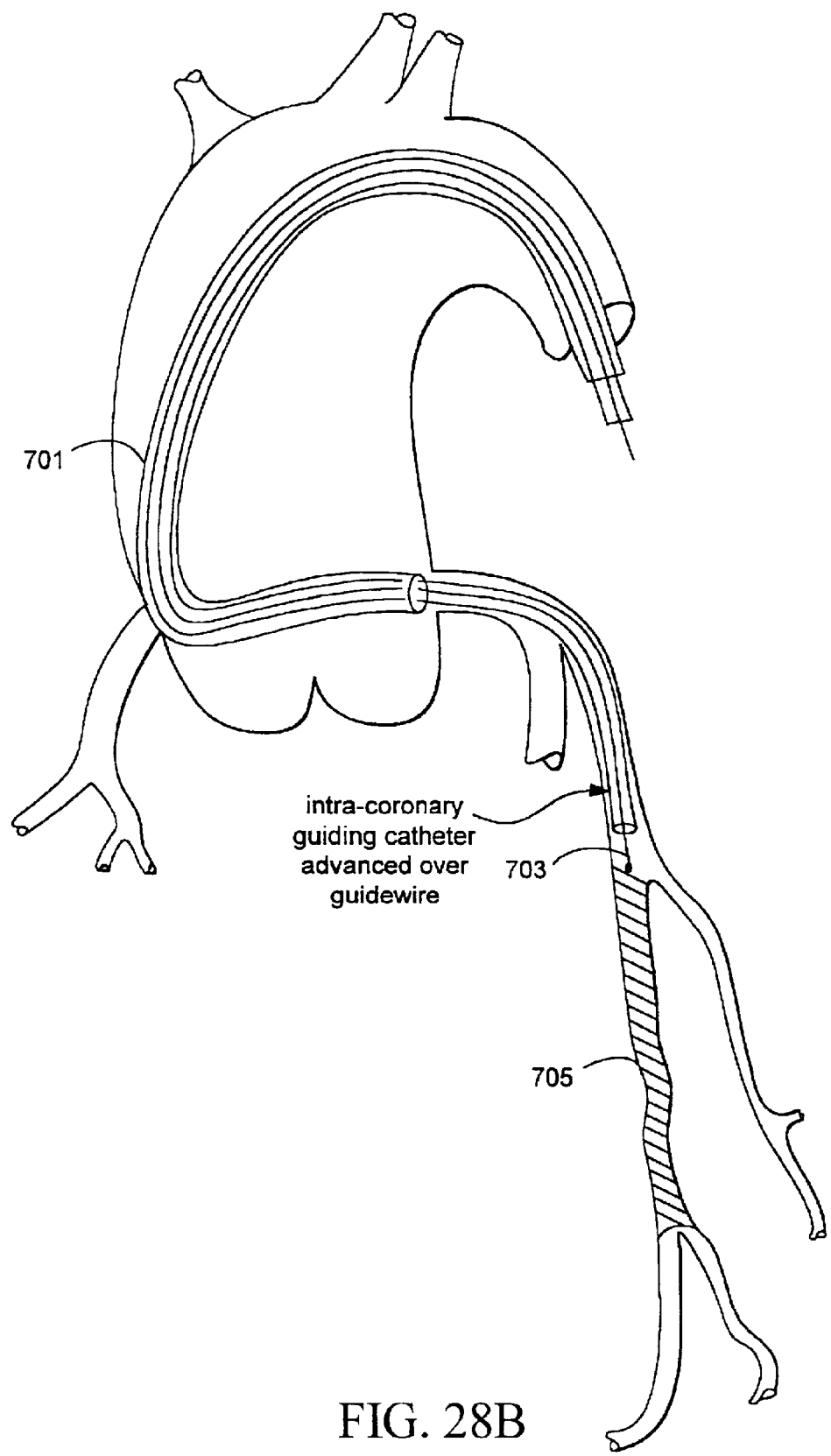
Figure 28C:
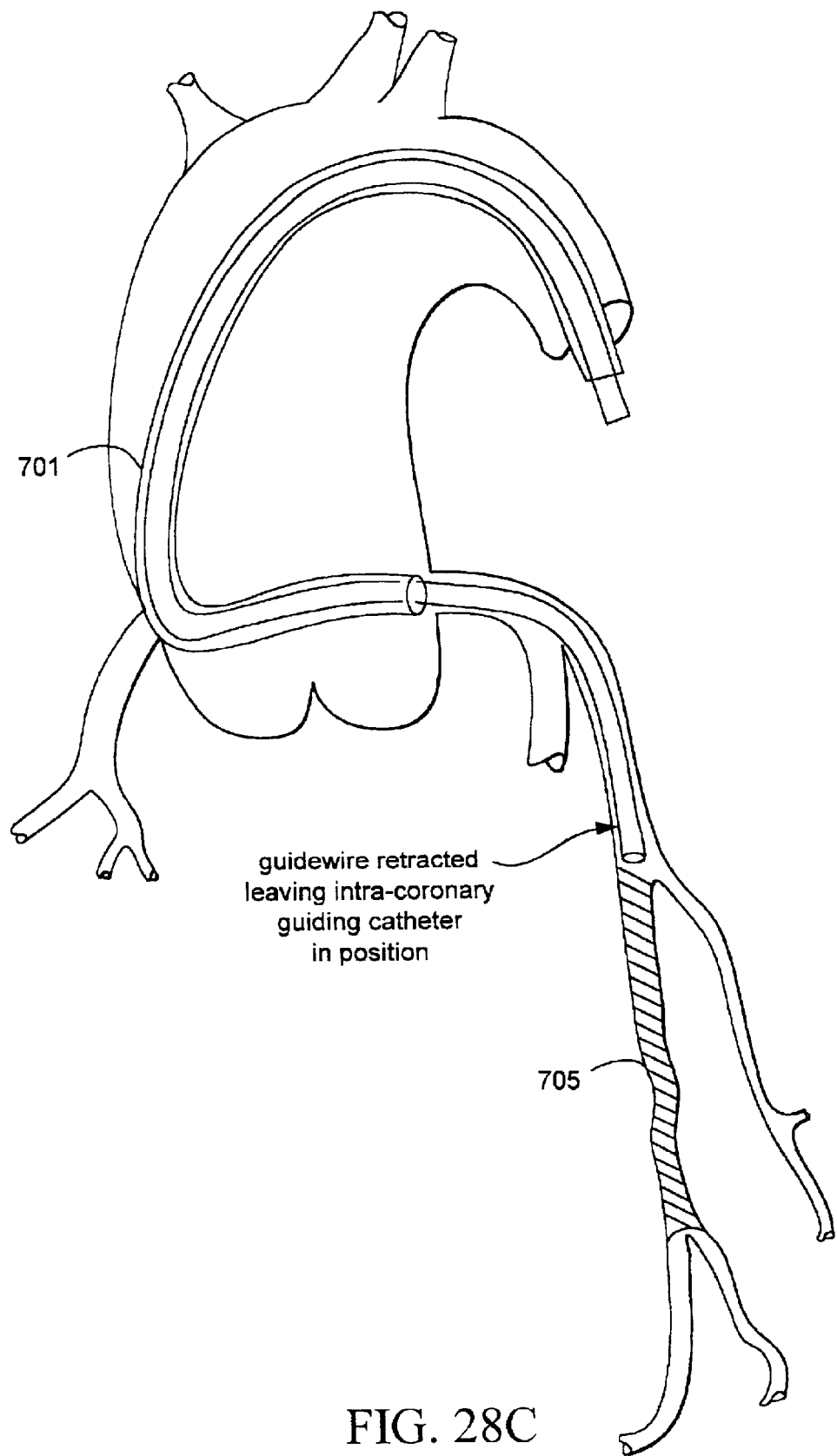
Figure 28D:
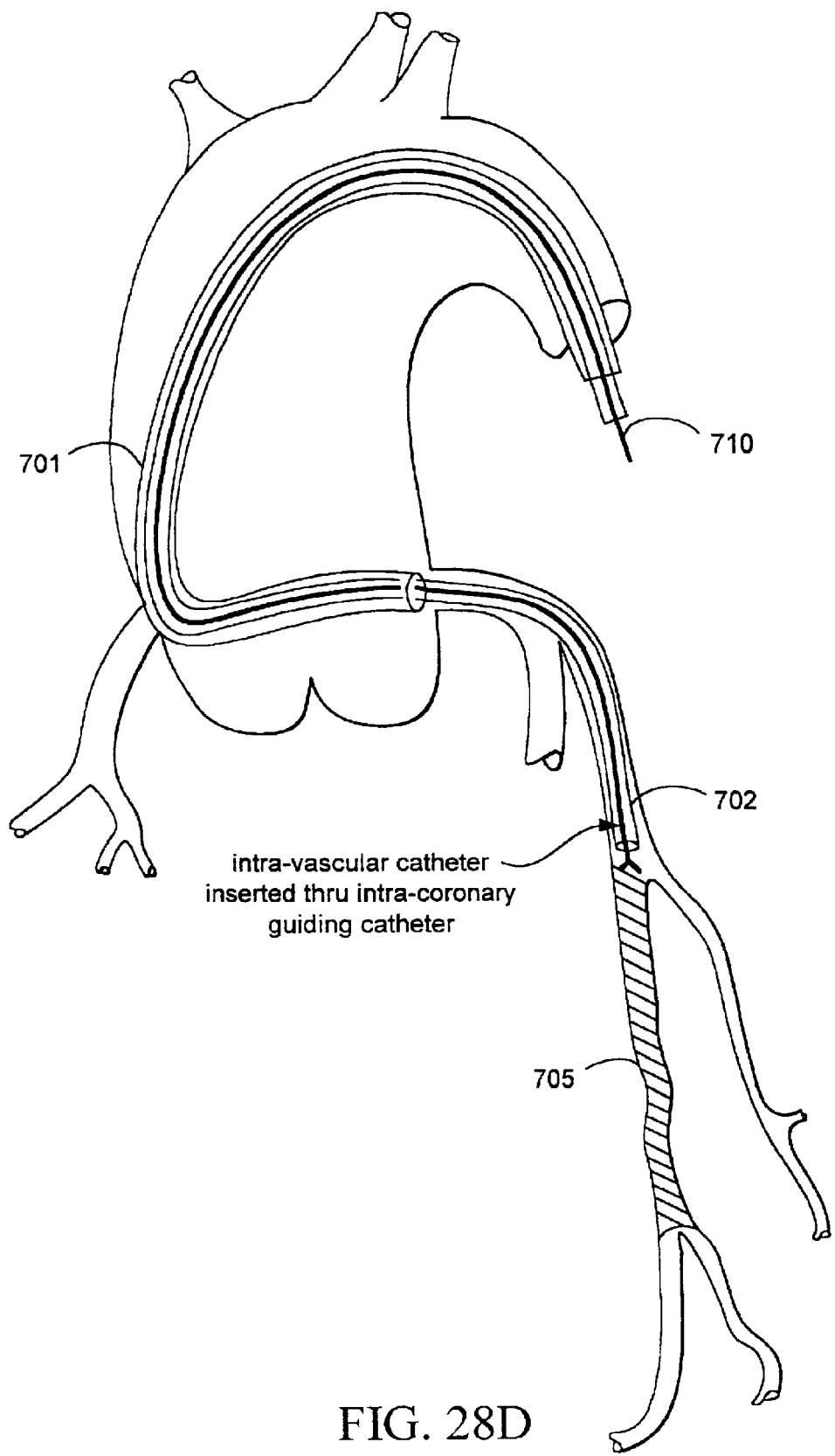
Figure 28E:
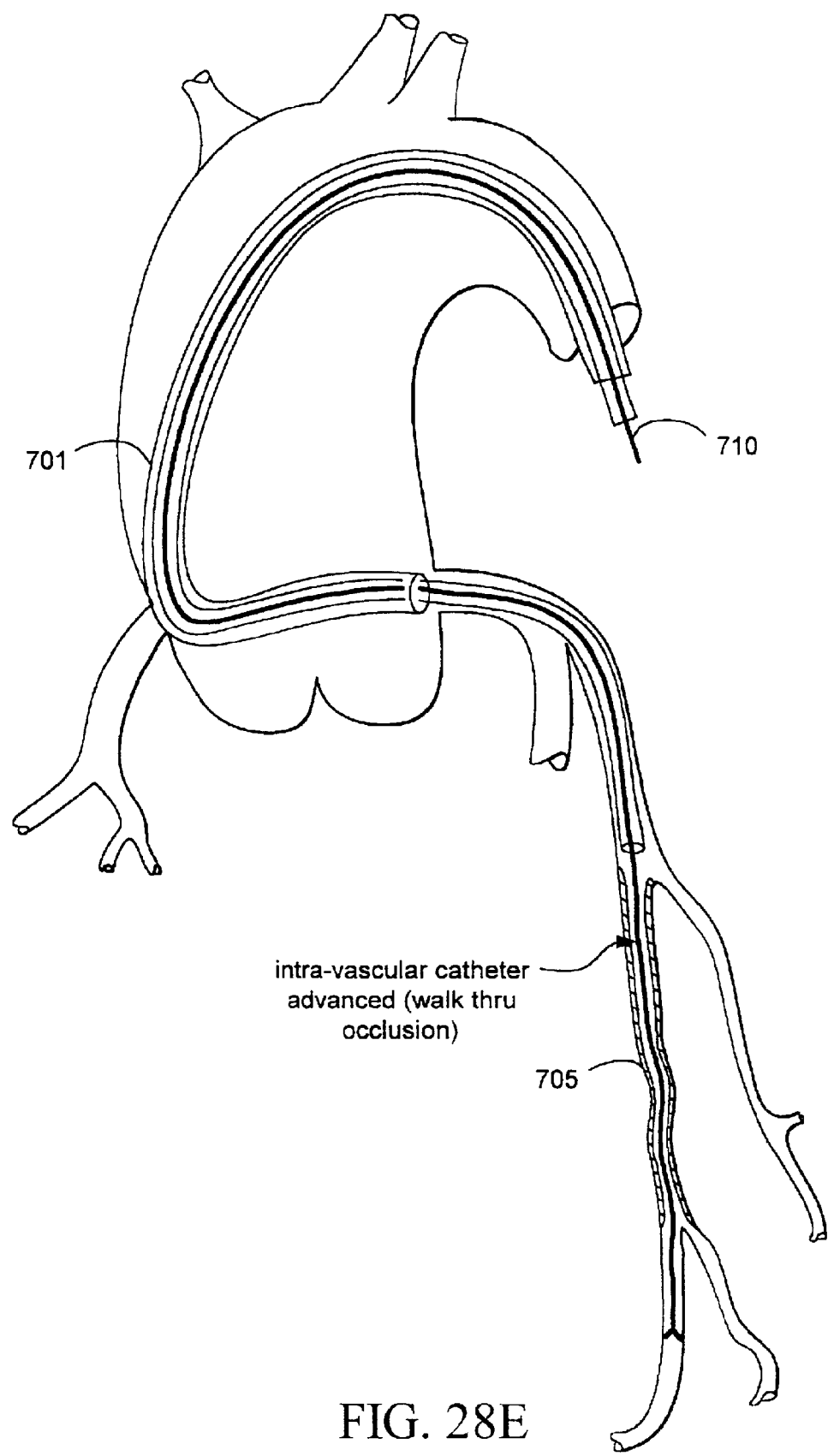
Figure 28F:
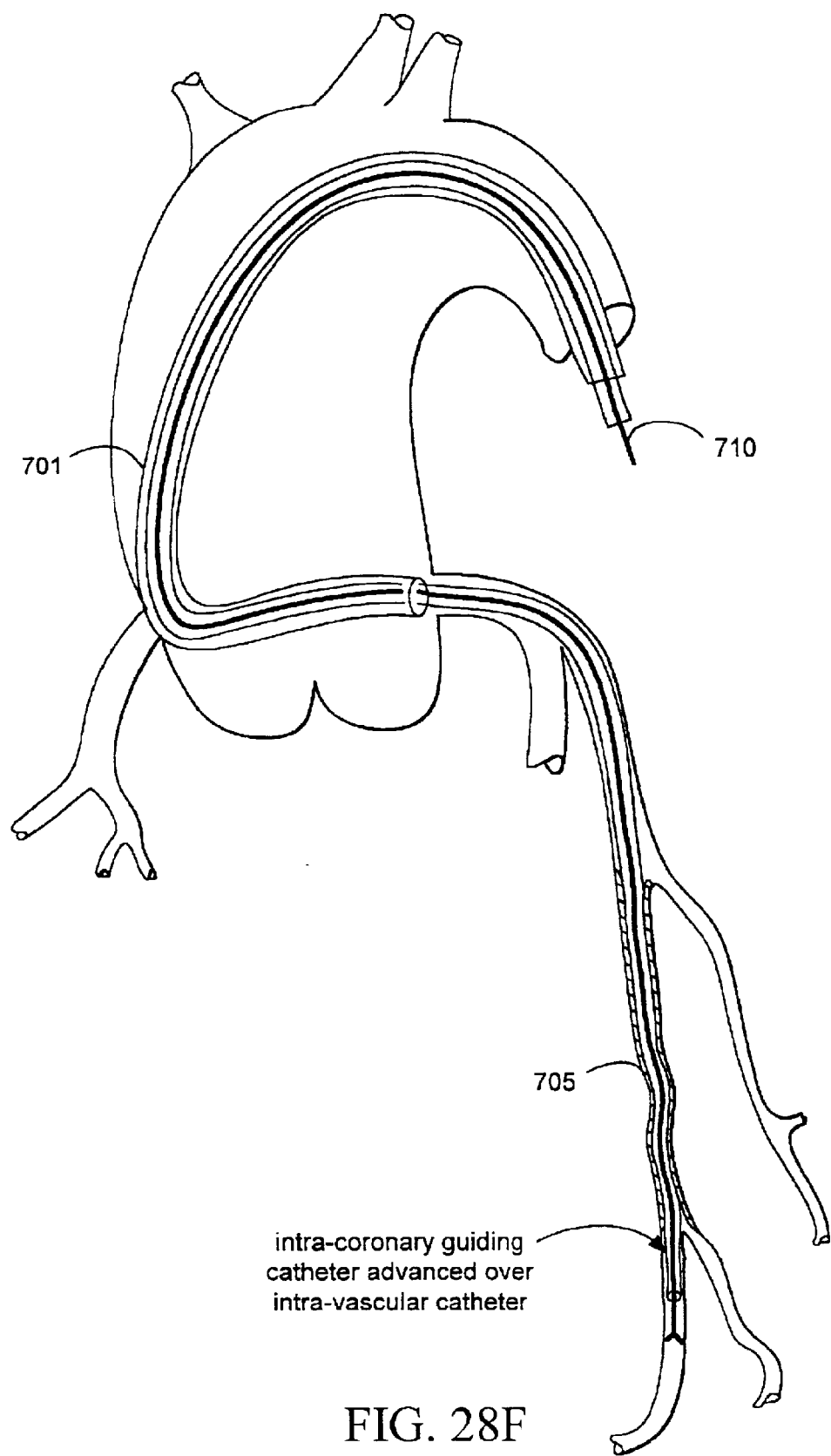
Figure 28G:
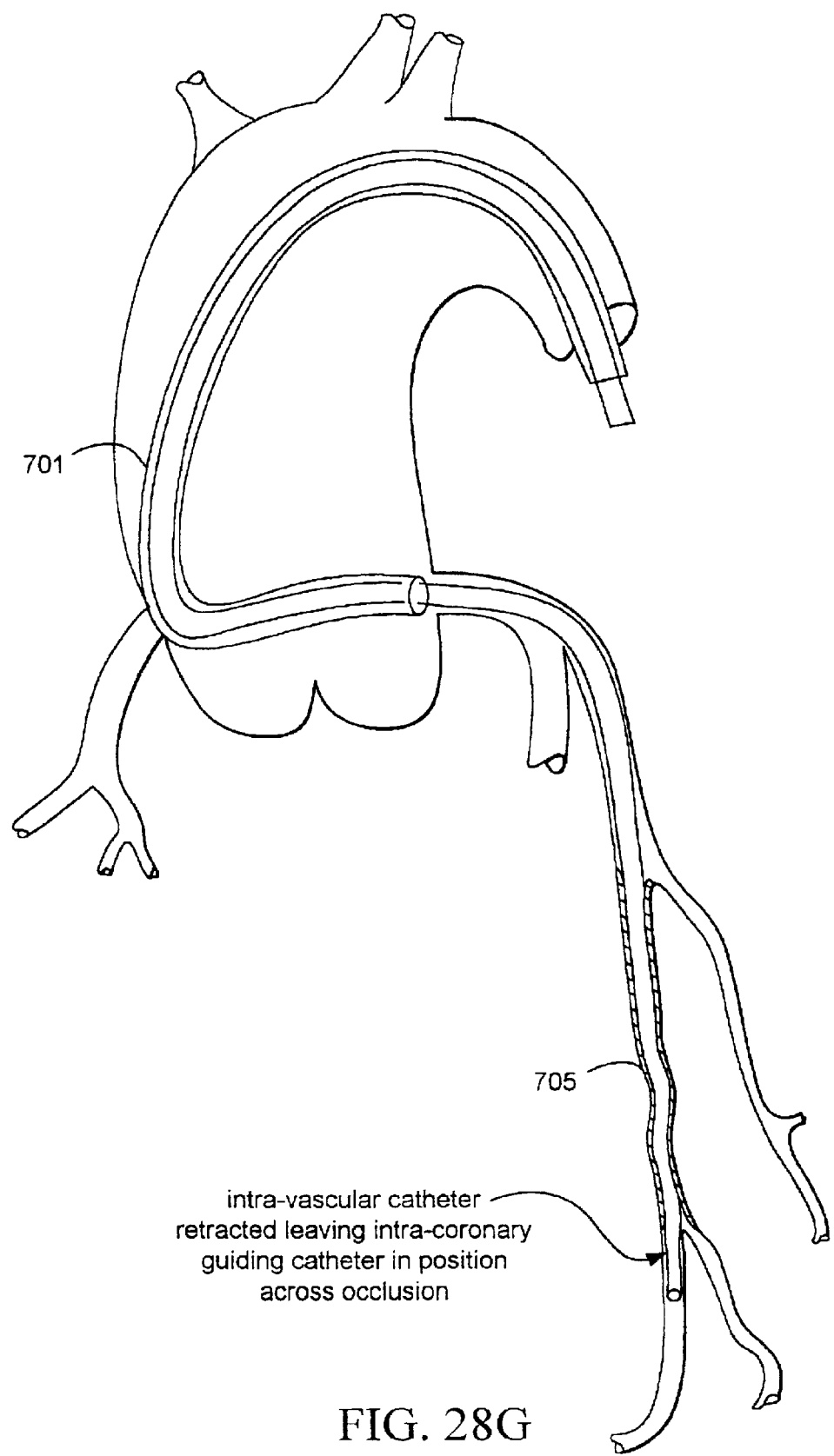
Figure 28H:
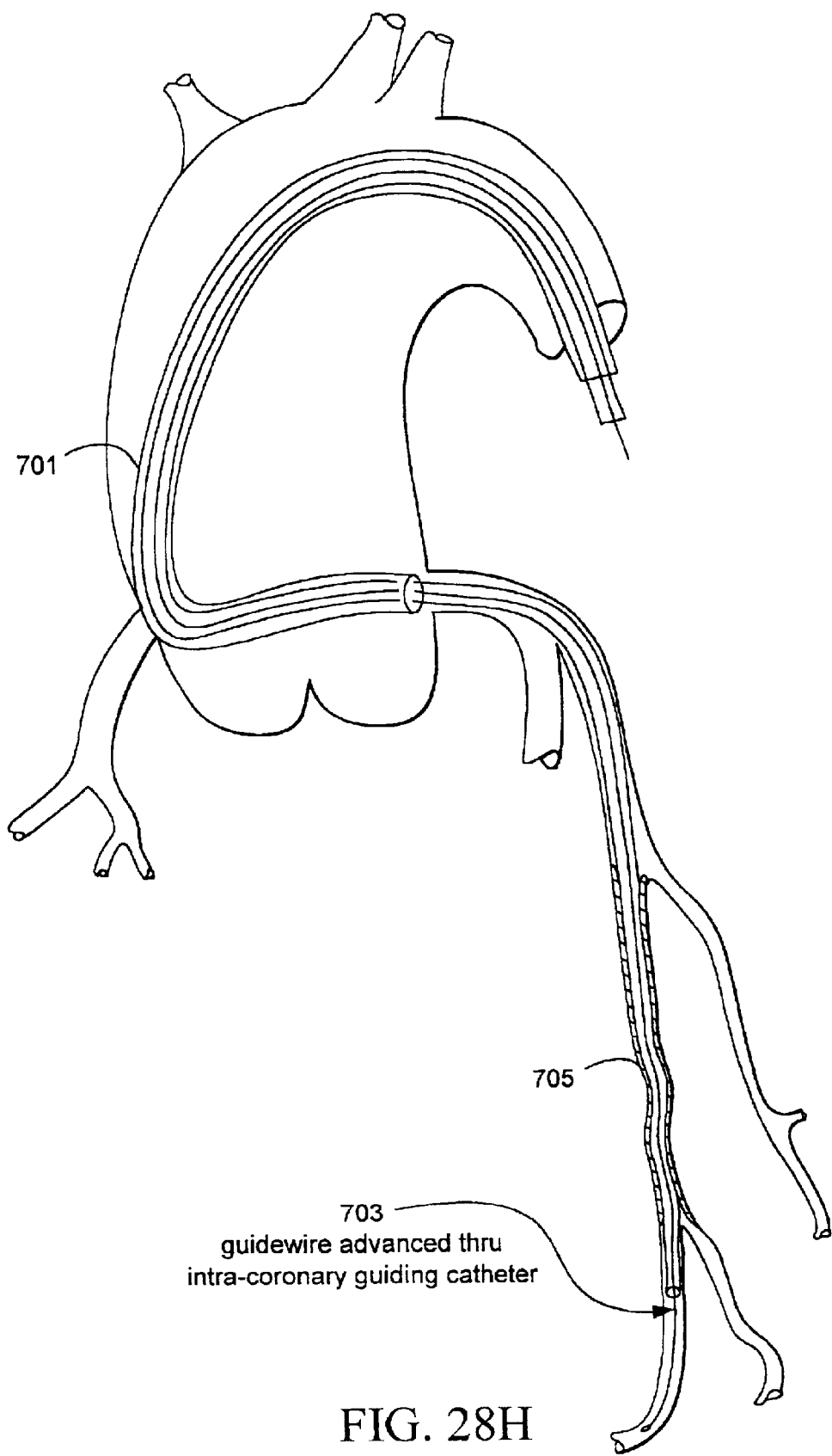
Figure 28I:
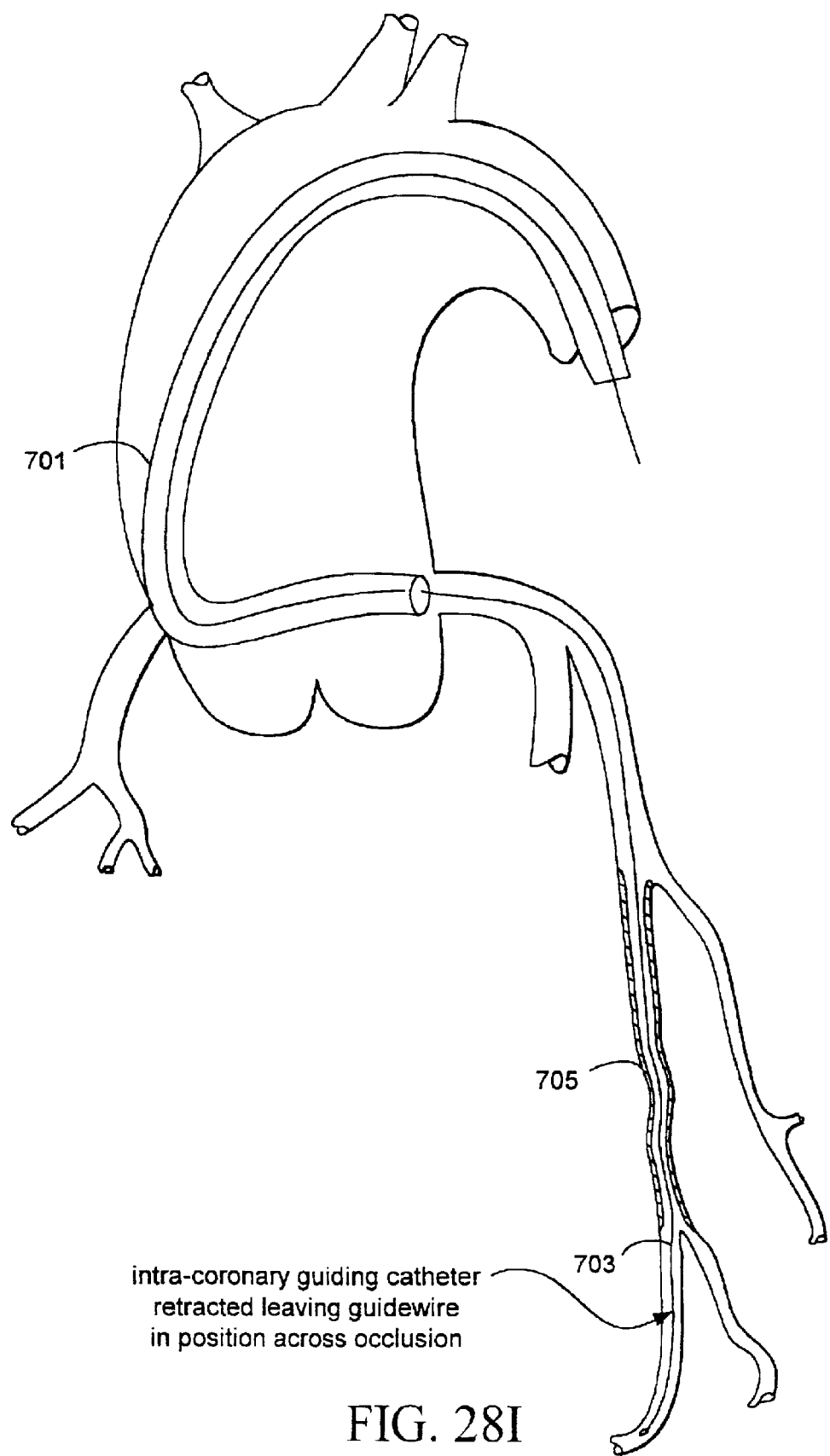

Another method of crossing a vascular occlusion involves the selection and advancement of a guidewire within a blood vessel to the site of a vascular occlusion. As shown in FIGS. 28A–B, a guiding catheter assembly 701 including an intra-coronary catheter 702 may be positioned over a guidewire 703 so that the distal end of the intra-coronary guiding catheter is in proximity or in contact with a vascular occlusion 705 such as a chronic total occlusion in the heart region. After removing the guidewire 703 from the blood vessel, as shown in FIG. 28C, an intravascular catheter 710 having at least one lumen may be inserted into the guiding catheter 701 within the blood vessel as shown in FIG. 28D. The intravascular catheter 710 may further include a spreading or tissue displacing member positioned at the distal region of the catheter that is responsive to directed force along the longitudinal axis of the catheter. An actuator assembly as described herein (not shown) may be positioned at least in part within the catheter 710 to transmit a directed force applied from the proximal portion of the catheter to the spreading member. The intravascular catheter may be advanced through the guiding catheter assembly 701 to position the spreading member of the intravascular catheter substantially adjacent to or at least partially within the occlusion 705. A directed force may be provided through the actuator assembly to spread apart the tissue displacing member in order to displace the tissue surrounding the vascular occlusion 705. The intra-coronary guiding catheter 702 and/or the intravascular catheter 710 may be advanced past the occlusion 705 before removal from the blood vessel as shown in FIGS. 28E–F. As shown in FIG. 28G, the intravascular catheter 710 may be retracted leaving the intra-coronary guiding catheter 702 in position across the occlusion 705. A guidewire 703 may be placed across, past or relatively distal to the displaced vascular occlusion 705 after or before removing the intravascular catheter 710 and/or a portion of the guiding catheter assembly 701 as shown in FIGS. 29H–I. It should be understood that any combination of one or more of the preceding steps may be performed or repeated in a variety of sequences to cross an occlusion located in any blood vessel.

While all aspects of the present invention have been described with reference to the aforementioned applications, this description of various embodiments and methods shall not be construed in a limiting sense. The aforementioned is presented for purposes of illustration and description. It shall be understood that all aspects of the invention are not limited to the specific depictions, configurations or relative proportions set forth herein which depend upon a variety of conditions and variables. The specification is not intended to be exhaustive or to limit the invention to the precise forms disclosed herein. Various modifications and insubstantial changes in form and detail of the particular embodiments of the disclosed invention, as well as other variations of the invention, will be apparent to a person skilled in the art upon reference to the present disclosure. It is therefore contemplated that the appended claims shall cover any such modifications or variations of the described embodiments as falling within the true spirit and scope of the invention.

What is claimed is:

1. A catheter for treating a vascular occlusion, comprising:
   an elongated shaft including a proximal section and a distal section, and at least one lumen extending from the proximal section to the distal section;
   two spreading members at the distal section of the elongated shaft, wherein each of the spreading members comprises a free distal end that moves laterally away from a longitudinal axis of the elongated shaft to disrupt the vascular occlusion; and
   an actuating assembly positioned along the elongated shaft to move the free distal ends of the two spreading members laterally in response to an actuation force, wherein the free distal ends of the spreading members are configured to apply a fracturing force to tissue including at least one of tissue of a blood vessel and tissue of the vascular occlusion and configured to support advancing the catheter through the tissue so that the tissue remains external to the catheter.

2. The catheter as recited in claim 1, wherein each of the two spreading members includes a cam follower on an interior of the spreading member.

3. The catheter as recited in claim 2, wherein the actuating assembly includes an actuation element including a distal end with a cam, wherein the cam is in contact with the cam follower to urge the spreading member in a substantially lateral direction.

4. The catheter as recited in claim 3, wherein the cam is configured as a central hub, and wherein the spreading member is urged in a substantially lateral direction when the cam is moved in a relatively proximal direction.

5. The catheter as recited in claim 3, wherein the cam is formed with an edge that slidably contacts the cam follower, and wherein the spreading member is urged in a substantially lateral direction when the cam is moved in a relatively distal direction.

6. The catheter as recited in claim 1, wherein the spreading member includes a substantially curved end.

7. The catheter as recited in claim 1, wherein the spreading member includes a substantially tapered end.

8. An intravascular tissue expanding catheter, comprising:
a catheter shaft formed of braided material, wherein the catheter shaft comprises at least one conduit extending along a longitudinal axis of the catheter shalt;
a housing formed at a distal end of the catheter shaft, wherein the housing includes two deflecting members that each comprise a free distal tip that moves in a lateral direction away from the longitudinal axis of the catheter shaft to expand intravascular tissue; and
an actuation assembly that moves the distal tips of the two deflecting members away from the longitudinal axis of the catheter shaft, wherein the distal tips of the deflecting members are configured to apply a fracturing force to the intravascular tissue including at least one of tissue of a blood vessel and tissue of the vascular occlusion and configured to support advancing the catheter through the intravascular tissue so that the intravascular tissue remains external to the catheter.

9. A catheter as in claim 8, wherein the two deflecting members each include an integrally formed hinge about which the distal tip of the deflecting member rotates.

10. A catheter as in claim 8, wherein the two deflecting members are each coupled to a discrete hinge about which the distal tip of the deflecting member rotates.

11. A catheter as in claim 8, wherein each of the two deflecting members includes an internal cam follower.

12. A catheter as in claim 11, wherein the actuation assembly includes a cam positioned within the housing for slidable movement along the cam followers of the two deflecting members to move the distal tips of the two deflecting members in a lateral direction.

13. A catheter as in claim 8, wherein the actuation assembly includes at least one pulling element coupled to the two deflecting members.

14. A catheter for use in vasculature, comprising:
a catheter body comprising at least one conduit extending through the catheter body;
two tissue expanding members coupled to a distal section of the catheter body, wherein each of the two tissue expanding members includes a proximal portion and a distal portion, and wherein the distal portion is free to move away from a longitudinal axis of the catheter body relative to the proximal portion; and
an actuation assembly within the catheter body such that when the actuation assembly contacts the two tissue expanding members, the distal portions of the expanding members move away from the longitudinal axis, wherein the expanding members are configured to apply a fracturing force to tissue including at least one of tissue of a blood vessel and tissue of a vascular occlusion and configured to support advancing the catheter through the tissue so that the tissue remain external to the catheter.

15. An intravascular catheter, comprising:
a catheter shaft including a distal end and a longitudinal axis having at least one lumen extending along the longitudinal axis of the catheter shaft;
an assembly at the distal end of the catheter shaft including two deflecting members each defined by a free distal tip that moves in a lateral direction away from the longitudinal axis of the catheter shaft to expand vascular tissue, wherein the two deflecting members are hinged to the catheter shaft; and
an actuating assembly positioned along the catheter shaft, the proximal movement of which moves the distal tip of the two deflecting members away from the longitudinal axis of the catheter shaft, wherein the deflecting members are configured to apply a fracturing force to tissue including at least one of tissue of a blood vessel and tissue of a vascular occlusion in the blood vessel and configured to support advancing the catheter through the tissue so that the tissue remains external to the catheter.

* * * * *